United States Patent
Thomas et al.

(10) Patent No.: US 7,672,712 B2
(45) Date of Patent: Mar. 2, 2010

(54) INTERNAL MARKER DEVICE FOR IDENTIFICATION OF BIOLOGICAL SUBSTANCES

(75) Inventors: Cherry T. Thomas, Cincinnati, OH (US); Richard L. Wahl, Ann Arbor, MI (US); Susan J. Fisher, Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 1872 days.

(21) Appl. No.: 10/624,261

(22) Filed: Jul. 22, 2003

(65) Prior Publication Data
US 2005/0004456 A1 Jan. 6, 2005

Related U.S. Application Data

(63) Continuation-in-part of application No. 09/539,002, filed on Mar. 30, 2000, now Pat. No. 6,628,982.

(51) Int. Cl.
*A61B 6/00* (2006.01)
*A61B 5/05* (2006.01)
*G01N 23/00* (2006.01)

(52) U.S. Cl. .................. 600/436; 600/420; 600/431; 250/308

(58) Field of Classification Search .......... 600/407, 600/420, 431–436, 458; 604/510, 529, 164.13; 250/308, 356.2, 363.03
See application file for complete search history.

(56) References Cited

U.S. PATENT DOCUMENTS

| | | | |
|---|---|---|---|
| 4,884,566 A | | 12/1989 | Mountz et al. |
| 5,067,162 A | * | 11/1991 | Driscoll et al. .............. 382/126 |
| 5,154,179 A | * | 10/1992 | Ratner ........................ 600/420 |
| 5,736,121 A | * | 4/1998 | Unger ........................ 424/9.4 |
| 5,766,151 A | * | 6/1998 | Valley et al. ........... 604/103.07 |
| 5,926,568 A | * | 7/1999 | Chaney et al. .............. 382/217 |
| 5,948,384 A | * | 9/1999 | Filler ........................ 424/1.29 |
| 6,162,648 A | * | 12/2000 | Maloney et al. ............. 436/178 |
| 6,175,760 B1 | | 1/2001 | Baskin et al. |

(Continued)

OTHER PUBLICATIONS

Wahl et al, "'Anatometabolic' Tumor Imaging: Fusion of FDG PET with CT or MRI to Localize Foci of Increased Activity," *J. Nucl Med.*; 34 (7); 1190-1197 (1993).

(Continued)

*Primary Examiner*—Eric F Winakur
*Assistant Examiner*—Michael T Rozanski
(74) *Attorney, Agent, or Firm*—Dierker & Associates, P.C.

(57) ABSTRACT

A device for visualizing structure located on the interior of a biological substance. The device includes a marker member that may be a solid cylinder or lumen having an interior volume having a distal end removably insertable in the biological substance relative to the interior structure to be visualized. An image-enhancing material is contained relative to the marker member in a manner such that the imaging material does not directly contact the biological substance. The imaging material of choice is one capable of producing an emission or signal detectable external to the biological substance by suitable imaging instrumentation. Also disclosed is a method for visualizing critical structures or radiation therapy targets in imaging processes such as positron emission tomography and/or single photon emission computerized tomography, MRI, or ultrasound either used alone or in combination or in registration with anatomical imaging processes such as computed tomography or mammography.

40 Claims, 8 Drawing Sheets

U.S. PATENT DOCUMENTS

| | | | |
|---|---|---|---|
| 6,177,675 B1 * | 1/2001 | Gagnon et al. | 250/363.1 |
| 6,226,418 B1 * | 5/2001 | Miller et al. | 382/294 |
| 6,303,935 B1 * | 10/2001 | Engdahl et al. | 250/363.03 |
| 6,309,634 B1 * | 10/2001 | Bankiewicz et al. | 424/93.2 |
| 6,351,573 B1 | 2/2002 | Schneider | |

OTHER PUBLICATIONS

Thorton et al., "A Head Immobilization System for Radiation Simulation, CT, MRI, and PET Imaging." *Medical Dolmetry;* 16; 51-58 (1991).

Brown et al., "MRI Imaging. Abbreviations, Definitions and Descriptions: A Review," *Radiology* 213 (3); 647-662 (1999).

Merkle et al., "MR Imaging—guided Radio-frequency Thermal Ablation in the Pancreas in a Porcine Model with a Modified C-Arm," *Radiology;* 213: 461-467 (1999).

Tilbury et al., "Reusable Gels for Germanium—68 Sources," *Appl. Radiation Trans.,* 42: 1111-1114 (1991).

Machtay et al., "Inaccuracies in Using the Lumpectomy Scar for Planning Electron Boosts in Primary Breast Carcinoma," *Int. J. Radiation Oncology Biol. Phys.,* 30: 43-48 (1994).

Regine et al., "Computer-CT Planning of the Electron Boost in Definitive Breast Irradiation," *I.J. Radiation Oncology,* 20: 121-125 (1990).

Forsberg et al., "Clinical Applications of Ultrasound Contrast Agents" *Ultrasonics,* 36: 695-701 (1998).

Magnevist Product Brochure, revised Dec. 1998.

* cited by examiner

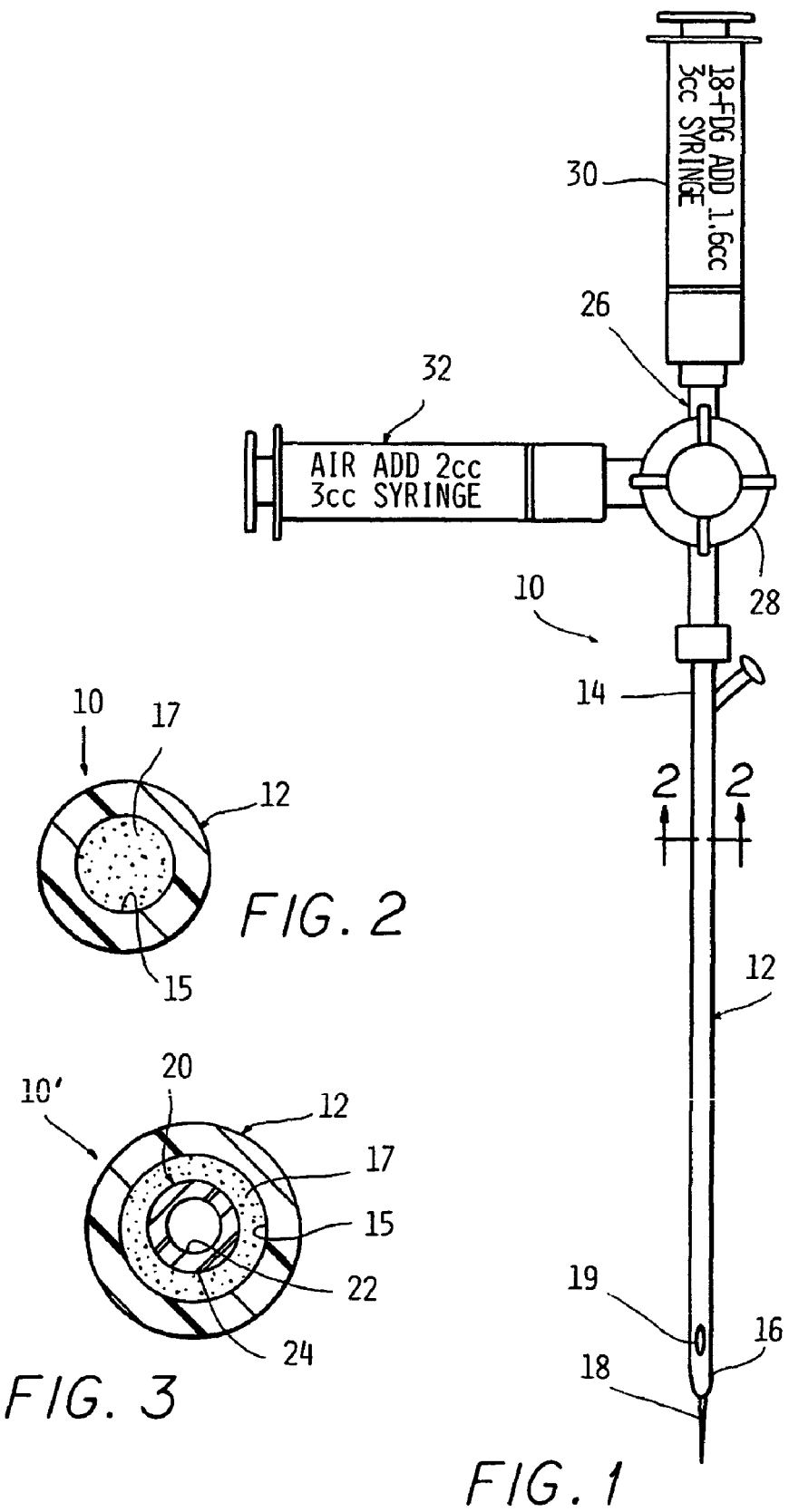

$V_A$ = VOLUME OF INJECTED AIR FROM SYRINGE $g$ = 10 m/s$^2$ $P_A$ = AIR PRESSURE ~ 10$^5$ N/m$^2$ $\rho$ = ASSUME ~ 1 g/cc → 10$^3$ kg/m$^3$

IN EQUILIBRIUM, FORCES ON FDG ALIQUOT ADD TO ZERO:

$$V_F \rho g + \pi r^2 P_T = \pi r^2 P_S \qquad (I)$$

$$P_T \pi r^2 Z = P_A V_A \quad (\text{II a})$$

SO $$P_T = \frac{P_A V_A}{\pi r^2 Z} \quad (\text{II b})$$

SO $$\underbrace{V F_\rho g}_{\substack{\text{FORCE} \\ \text{DUE TO} \\ \text{GRAVITY} \\ (F_g)}} + \underbrace{\frac{P_A V_A}{Z}}_{\substack{\text{FORCE} \\ \text{PUSHING} \\ \text{DOWNWARD} \\ \text{ON FDG} \\ \text{DUE TO} \\ \text{PRESSURE} \\ \text{IN THE TUBE} \\ (F_T)}} = \underbrace{\pi r^2 P_S}_{\substack{\text{FORCE} \\ \text{PUSHING} \\ \text{UPWARD} \\ \text{DUE TO} \\ \text{STOMACH} \\ \text{PRESSURE} \\ (F_S)}} \quad (\text{III})$$

*FIG. 5A*

AS AIR IS INJECTED, THE ALIQUOT OF FDG MOVES DOWN THE TUBE AND $Z$ IS GIVEN BY:

$$Z = \frac{P_A V_A}{\pi r^2 P_S - V F_\rho g} \quad (\text{IV})$$

NOW $$V F_\rho g \leq (2\,cc)(1\,g/cc)(10\,m/s^2)$$

$$\leq 2 \times 10^{-2}\,N \quad \textit{gravitational force}$$

AND $$\pi r^2 P_S \sim (3.14)(1.27\,mm)^2 (10^5\,N/m^2)$$

(ASSUMING $P_S \sim$ AIR PRESSURE)

$$\sim 5.1 \times 10^{-1}\,N \quad \textit{force from stomach}$$

*FIG. 5B*

INTERNAL MARKER DEVICE FOR IDENTIFICATION OF BIOLOGICAL SUBSTANCES

CROSS-REFERENCE TO RELATED APPLICATIONS

This application is a continuation-in-part of U.S. Ser. No. 09/539,002 filed Mar. 30, 2000, now U.S. Pat. No. 6,628,982.

STATEMENT OF GOVERNMENT SUPPORT

This invention was made in the course of research partially supported by a grant from the National Institute of Health (NIH CA 52880). The U.S. government has certain rights in the invention.

FIELD OF THE INVENTION

The present invention is related to identifying landmarks that assist in visualizing internal structures during diagnostic and/or therapeutic procedures, including medical procedures.

BACKGROUND OF THE INVENTION

Targeting aids or landmarking devices have been employed in diagnostic imaging techniques such as computed tomography (CT), magnetic resonance imaging (MRI) and ultrasound. These devices, commonly referred to as fiducial markers, generally occur as two types: internally occurring markers that are inherent in the subject's anatomy; and externally positionable imaging aids that can be permanently or temporarily affixed to the body under analysis. External fiducial markers have also been proposed for use and have been used in other imaging techniques such as positron emission tomography (PET) and single photon emission computed tomography (SPECT) as well as in imaging techniques such as MRI and CT. No effective internally positionable devices have been developed.

Imaging techniques such as PET and SPECT rely upon cellular uptake of suitable imaging solutions such as 2-deoxy-2-[$^{18}$F]fluoro-D-glucose to provide accurate images of metabolically active tissue, including cancerous or abnormal tissue material. Malignant cells, such as those found in cancerous tumor tissue, generally exhibit elevated energy requirements resulting in elevated levels of glucose consumption or other functional processes. By comparison, surrounding tissue is less metabolically active. Imaging techniques such as PET make use of this differential in cellular glucose uptake or functional or molecular uptake by employing radiopharmaceutically tagged uptake solutions to demonstrate areas of interest for imaging and analysis. SPECT and PET with other radiotracers such as $^{18}$F-fluorodeoxyglucose, $^{18}$F-sodium fluoride, $^{11}$C-methionine, $^{11}$C-choline, $^{11}$C-acetate, $^{18}$F-fluorocholine, $^{18}$F-fluoroethylcholine, $^{11}$C-deoxyglucose, $^{15}$O-oxygen, $^{11}$C-carbon monoxide, $^{15}$O-water, $^{11}$C-butanol, $^{11}$C—N-methylspiperone, $^{18}$F—N-methylspiperone, $^{18}$F-spiperone, $^{11}$C-flumazenil, $^{11}$C-ACHC, $^{11}$C-tyrosine, $^{11}$C-thymidine, $^{18}$F-beta estradiol, 16 alpha $^{18}$F-fluoroestradiol, $^{18}$F-moabs can image, for example, regional glucose metabolism, bone tumors, amino acid uptake and protein synthesis, cell membrane proliferation, regional brain metabolism, metabolic rate of oxygen utilization, blood flow and proteins. While both PET and SPECT allow distinction of tumor from normal tissues, there are instances in which PET and SPECT are difficult to use as a single imaging modality.

One drawback of such radiopharmaceutically assisted imaging techniques is that the visualized area of increased tracer accumulation is best localized in comparison to known anatomical references in order to be precisely characterized and located in the subject's body. In order to be visualized in a PET or SPECT scan, the anatomical element of interest must also be capable of sufficient uptake of radioactivity to provide a detectable emission. Thus, localization can be accomplished using PET or SPECT when a known anatomical landmark also exhibits increased radiotracer uptake relative to the surrounding imaged tissues. In such instances, the landmark can provide a reference against which the region under study can be located, analyzed and measured. This requirement becomes problematic in regions of greater anatomical variation, and in regions which have little radiotracer uptake on scan. Such regions provide few reference landmarks which have levels of increased cellular glucose or other tracer uptake.

This problem becomes more pronounced in situations where imaging data generated from PET or SPECT scans are to be integrated with imaging data derived from other methods such as, e.g., MRI, CT, or ultrasound. As described in Wahl et al., "Anatometabolic Tumor Imaging: Fusions of FDG PET with CT or MRI to Localize Foci of Increased Activity," J. Nucl. Med; 34 (7); 1190-1197, (1993) "metabolic" data generated from PET studies of specific anatomical regions have been fused with imaging data generated by MRI and/or CT to visualize "hot spots" generated by abnormal cellular activity. Such data have been registered to anatomical images generated by MRI and/or CT. In Thornton et al., "A Head Immobilization System for Radiation Simulation, CT, MRI, and PET Imaging," Medical Dosimetry: 16; 51-56, (1991), contour tubing is permanently mounted to immobilizing masks used in simulation planning and during radiation treatment for both central nervous system and cranial and facial tumors. A suitable positron emission material such as a fluorine-18 solution is inserted in the tubes to provide a positron emission from the known external source. The authors describe an external marker system that provides a reference system for imaging correlation.

In the process described in the Wahl et al. reference, external fiducial markers were placed during both anatomic (CT and MRI) and metabolic (PET) studies. These external fiducial markers, as well as inherent internal anatomical landmarks, were used to reconstruct fused images from the various imaging studies. This permitted greater accuracy in localizing structures of interest.

U.S. Pat. No. 4,884,566 to Mountz et al. is directed to an externally positioned apparatus for defining a plane of an image through a portion of the body. The device includes a frame onto which a plurality of channels can be mounted. A suitable imaging material can be contained in the channels to provide reference markers during scanning.

The methods and devices described in the Wahl and Thornton references present difficulties when employed to visualize regions where greater patient-to-patient anatomical variation is encountered. Such regions often lack internal landmarks or accurate correlation with the positioning of external fiducial markers. The device disclosed in Mountz has an effective use in imaging more confined and rigid regions like the cranium. However, external devices such as the Mountz device or that disclosed in Thornton are not designed for marking internal imaging regions such as the chest, abdomen or pelvis. In addition, external markers do not localize deep anatomy.

In three-dimensional radiation treatment planning or intensity-modulated radiation therapy, the ability to visualize targets and critical structures is crucial. These critical structures are organs that receive radiation dose but are not themselves targets for treatment. Examples of critical structures include, but are not limited to, the optic chasm, esophagus, spinal cord, small and large bowels, rectum, kidneys, vaginal walls, etc. Knowledge of the location of critical structures, as well as the targeted tissue for treatment, permits more accurate targeting and precise administration of radiation dose and greater sparing or normal tissue radiation toxicity.

The problem can present in many situations, for example, when functional imaging is introduced into radiation treatment planning for thoracic cancers such as lung cancer. In such situations it is important to visualize critical structures, such as the esophagus, in a manner that will permit the radiation oncologist to locate and identify critical structures and to locate the target tissue to plan and administer therapeutic radiation dose in a precise and accurate manner. Critical structures, such as esophageal tissue, are difficult to visualize in PET due to relatively low metabolic uptake of radiopharmaceutically marker by the esophagus, particularly in relation to the target tumor. Under such circumstances, metabolic emission imaging techniques such as PET or SPECT are of limited utility.

References such as Wahl et al. have proposed fusing data produced from metabolic imaging techniques with data generated from other imaging techniques. However, accurate visualization of certain critical structures or targets can be difficult even in multiple imaging systems. MRI is particularly sensitive to moving tissue. Even a stationary-positioned patient will produce motion from breathing, heart rate or peristalsis which can create image displacement or edge blurring artifacts. MRI motion artifact correction techniques such as retrospective triggering and respiratory compensation as well as gradient motion compensation do not completely remove motion artifacts from an MRI image, (Brown et al. "MRI Imaging, Abbreviations, Definitions and Descriptions: A Review," *Radiology* (1999) 213 (3): 647.) Deep anatomy fiducial markers can facilitate inclusion of MRI imaging in multi-imaging modality fusion by complementing existing MRI artifact correction techniques.

The sensitivity and specificity of ultrasound is limited when applied to the study of small and deep anatomic structures. The utility of ultrasound imaging for multimodality image fusion would be enhanced through the use of an internal fiducial marker containing contrast agents that produce a homogeneous transmission of sound, harmonics or echogenicity. When targets and critical structures can be visualized by imaging techniques such as but not limited to PET, SPECT, MRI, ultrasound, CT or mammography, the ability to obtain fused multi-imaging data is limited, due, in part, to the absence of effective constant landmarks such as internal fiducial markers.

Based on the limitations of the imaging modalities described above, it is desirable to have means for more accurately identifying internal critical structures in various imaging techniques. It is also desirable to provide utility for maximum use of existing techniques for demonstrating morphologic and molecular disease. This is one of the research priorities of the U.S. National Institutes of Health.

SUMMARY OF THE INVENTION

In one aspect, the present invention is directed to a device for visualizing structure located in the interior of a substance that is visually opaque. As used herein, the term "visually opaque" is taken to mean obscure or not apparent using characteristic imaging modalities. The present invention provides a method and apparatus based on removably positionable internal fiducial markers as a targeting aid or a landmarking or verification device for various imaging techniques. The device is capable of being removably inserted into a suitable lumen or cavity in the subject to be scanned or imaged. The device contains a material detectable by imaging techniques, and such material is capable of emitting a detectable reference signal relative to the focus of the imaging scan. More particularly, the device, which is removably inserted into a subject and emits a detectable signal by one or more imaging modalities, assists in visualizing an internal organ structure, and assists in the positioning, localization and imaging of tissue or cell clusters of interest within a visual field that encompasses the removably positionable device and the tissue of interest during scanning or imaging procedures.

The device of the present invention includes at least one removably insertable marker member which, when in place in the desired region of the body to be imaged, will act as a suitable fiducial marker for the type of scan or scans to be performed. The removably insertable marker member may be a solid member or may have a suitably configured void space located therein. This void space may be either a hollow cavity defined in one region of the marker member or it may be a hollow conduit running at least partially through the length of the marker member such as a lumen. The body of the marker member may be either flexible or suitably rigid, depending on the nature of the anatomical structure to be visualized.

The marker member has a proximal end and a distal end. The distal end of the marker member is removably insertable in the visually opaque substance relative to the internal structure to be visualized. The body of the marker member is composed of a biologically stable substrate material. As used herein, the term "biologically stable substrate" is a material which will remain essentially non-interactive with the visually opaque substance to be visualized or the system or organism in which the opaque substance is contained. The biologically stable substrate material may be one which can produce an MRI, positron or ultrasound signal. Preferably at least one imaging material is contained in the lumen in a manner which prevents the imaging material from direct contact with surrounding visually opaque substance. The imaging material of choice is one which is capable of producing an emission detectable external to the visually opaque substance. It is also within the scope of this invention that the solid substrate material may be one that can produce an MRI, positron or ultrasonic signal. The visually opaque substance is, preferably, a biological substance and, most preferably, an anatomical structure as would be found in a human or other mammal. The imaging material may be a substance which is capable of magnetic resonance, visually dense under ultrasonic or x-ray scanning or capable of emitting detectable emission such as radiopharmaceutical imaging material.

The entire apparatus or portions thereof may produce the relevant signal for imaging. That is to say that the marker member can be a solid that is composed, at least in part, of a material suitable for use in the imaging modalities enumerated previously. This solid may be imaging material itself or may be a solid that may suitably contain the desired imaging material through at least a portion of the body of the device. The imaging material, when contained on a portion or segment of the body of the marker member, may be positioned on a discrete region or regions. The positioning of the imaging material may be transverse on the body of the device or may be located on discrete longitudinal region or regions, depending on the requirements of the imaging procedure.

In an alternative, the marker member may be composed of at least one lumen. The lumen may be suitably flexible, partially flexible, or possess the degree of rigidity desired or required by the particular tissue or anatomical region under analysis.

The present invention is also directed to a process for visualizing difficult-to-visualize critical structures through a method that employs the removable device of the present invention. In the contemplated method, the removable device of the present invention is inserted into position in the interior of a physical cavity integral in the visually opaque substance. Emissions generated from the imaging material or changed sonographic or magnetic resonance signal characteristics resulting from the imaging material contained in the device of the present invention are recorded and localized. Any emission signal generated from any other regions of the visually opaque material are also recorded and localized. Emission signals recorded and localized are integrated into translatable data. After the data has been obtained, the visualizing device and all imaging source material contained therein are removed from the interior of the visually opaque substance.

BRIEF DESCRIPTION OF THE DRAWINGS

To further illustrate the present invention, the following drawing is included in which:

FIG. 1 is a side view of a visualizing device constructed according to one embodiment of the present invention;

FIG. 2 is a cross-sectional view of the visualizing device taken along the 2-2 line of FIG. 1;

FIG. 3 is a cross-sectional view of an alternate embodiment of the visualizing device of the present invention having two concentrically disposed lumina;

FIG. 5A is a mathematical representation of the physical forces that hold the imaging material in position in the device of FIG. 1 at equilibrium;

FIG. 5B is a mathematical representation of physical forces acting on the imaging material as air is introduced into the lumen of the device of FIG. 1;

DETAILED DESCRIPTION OF THE PREFERRED EMBODIMENTS

Figure 4:
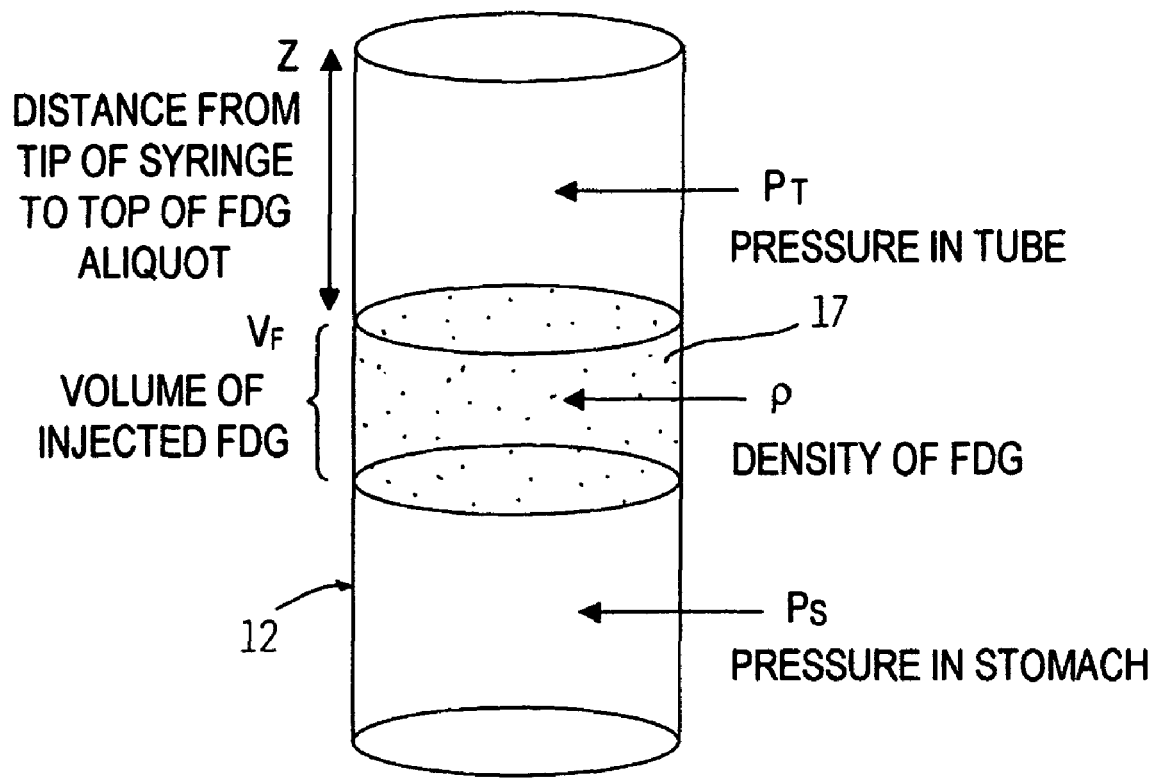
FIG. 4 is a graphic representation of the physical forces which hold the imaging material in position in the device of the present invention.

The present invention addresses the problems related to visualizing targets or critical structures using various imaging modalities. Furthermore, the present invention also addresses problems relating to correlating various imaging modalities. The device of the present invention may be employed to produce a depiction of the molecular, biological, anatomical or other regions of interest generated using one or more imaging modalities.

It is to be considered within the purview of this invention that the visualizing device can be employed to assist in the visualization of any visually opaque substance which is analyzable by processes such as positron emission tomography (PET), single photon emission computed tomography (SPECT), magnetic resonance imaging (MRI), ultrasound imaging, or computed tomography (CT). Even more specifically, the device of the present invention can be used to provide functional PET, SPECT, MRI, CT, or ultrasound images that can be used alone or correlated with any one of the other techniques. The present invention provides means by which the various images, with their distinct appearances, can be accurately correlated or verified in a manner which permits reproducibility of image planes in the x, y and z directions.

Other systems and media in which the device and methodology of the present invention can be advantageously employed are not limited to human and/or mammalian systems. Other uses for the present invention will become apparent to the skilled artisan upon reading the present disclosure.

The present invention is a device for visualizing structure located on the interior of a substance that is visually opaque. The substance subject to such analysis will be one that is readily amenable to at least one imaging technique. Such techniques include, but are not limited to, PET, SPECT, ultrasound, MRI and/or CT. Other imaging techniques that elucidate the interior of the visually opaque substance could potentially be employed using the device of the present invention.

The visually opaque substance to be analyzed is, preferably, a biological substance having at least one interior channel defined therein and having at least one structure which is not routinely visualizable by the imaging technique employed. Even more specifically, the visually opaque substance of the present invention is a biological anatomical system such as a human being, higher mammals, or other multicellular organisms. The structure to be visualized using the device of the present invention can be any organ channel, or structure of interest. Of particular interests visualization of potential spaces in a body or body cavity. As used herein, the term "potential space" is defined as an organ cavity or region of flexible or variable volume and/or some limited movability within the body or body cavity. Examples of potential spaces in human anatomy include, but are not limited to, organs such as the esophagus, stomach, rectum, bladder and vagina.

In instances of radiation treatment planning, the structure to be visualized can be a critical structure or a related anatomical feature proximate thereto. As used herein, the term "critical structure" is defined as organs or tissues which receive radiation dose but are not targets for radiation treatment. Accurate knowledge about the location and configuration of critical structures can provide valuable information for planning radiation therapy radiation dose or dose escalation and reducing normal tissue toxicity.

In instances of radiation treatment planning, the structure to be visualized can be a target. As used herein, "target" is defined as a structure or tissue which is specified or prescribed to receive primary radiation dose. An example of the use of the present invention for identification of targets includes, but is not limited to, a thin esophageal, rectal, vaginal or endometrial cancer not well seen by PET. The device of the present invention can advantageously be employed to help localize tumor regions for optimal beam arrangements. This device of the present invention has particular utility when multiple images modalities are used as can occur in diagnostic radiology or radiation treatment planning.

The device of the present invention can be advantageously employed with various imaging techniques. It is envisioned that the device of the present invention can be used to emit a suitable detectable signal which is detectable exterior to the visually opaque substance. Detection can be by any suitable known method and process.

The device of the present invention may be used for locoregional treatment modalities where normal tissue toxicity considerations are paramount. These modalities include, but are not limited to, hyperthermia, brachytherapy, laser ablation, radio frequency ablation, cryotherapy, proton beam therapy and neutron beam therapy. One specific example, which is not to be construed as limitative of the scope of the present invention, is the use of the device of the present invention for magnetic resonance imaging-guided radio-frequency ablation of targets. Magnetic resonance images such as those discussed in Merkle et al, "MR Imaging-guided Radio-frequency Thermal Ablation in the Pancreas in a Porcine Model with a Modified C-Arm," *Radiology* (1999; 213: 461-467) can be fused with PET, CT, or ultrasound with the device of the present invention for more accurate localization for therapeutic intervention. Localization of targets, critical structures or tissues a physician may wish to avoid may be enhanced with the device of the present invention in the aforementioned treatment modalities.

As used herein the term "suitably detectable signal" is taken to refer to a reference which can be detected or translated by a suitable externally positioned visualizing or detection device. It can be understood that there are many ways in which the device of the present invention can be used to emit or produce a suitably detectable signal applicable for the chosen modality.

It is anticipated that the visualizing device can be employed to provide a landmark or as a direct localizing orientation means for use in conjunction with an imaging technique such as PET, SPECT, or other analogous methods and, as such, will be capable of providing a positron emission detectable exterior to the visually opaque substance.

It is anticipated that the visualizing device will be employed to provide a landmark or direct localizing or verification means for use in conjunction with a technique such as ultrasound or other analogous methods, and, as such, will be capable of providing echo signals which will improve the signal-to-noise ratio producing, in turn, ultrasound contrast only imaging.

It is anticipated that the visualizing device can be employed to provide a landmark or as direct localizing or verification means for use in conjunction with a technique such as MRI or other analogous methods, and as such, capable of providing a local magnetic field which can re-emit radio waves which can be received and used for reconstruction of a magnetic resonance image.

The device of the present invention may be used with such position detection methods either alone or in conjunction with one or more imaging methods in any combination and in combination with CT. It is to be understood that, in its broadest sense, the device of the present invention is not limited to use with any one imaging technique but could be employed successfully to visualize structure in many other imaging techniques either alone or in combination with one another.

The device of the present invention visualizes structures located on the interior of a visually opaque substance. The device of the present invention may be made of either rigid or flexible construction or a suitable combination of the two, as required, for successful removable insertion into a visually opaque substance. It is also within the scope of this invention that the device of the present invention be imbued with temporary rigidity sufficient to accomplish successful insertion and/or proper placement. One such manner of rendering temporary rigidity will be described subsequently.

In one embodiment, as depicted in FIGS. 1 and 2, the device 10 includes as a marker member, a flexible tubular lumen 12 which has an elongated central interior defined by a cylindrical wall 15. The flexible lumen 12 has a proximal end 14 and a distal end 16. The lumen 12 contains a suitable imaging material 17 in at least a portion of the central interior. The imaging material 17, as broadly contemplated in the present invention, may be any material which will produce a discernable image or assist in the production of a discernable image when subjected to one of the various scanning techniques described herein. The imaging material can be one that is echogenic, as would be the case with ultrasound imaging. For x-ray processes, and specifically for CT, the imaging material will possess a linear attenuation coefficient in excess of that of water. The imaging material can be one in which a discernable magnetic resonance or magnetic moment can be induced, as would occur in MRI. A radiopharmaceutical imaging material capable of producing an emission detectable external to the visually opaque substance can be employed. The radiopharmaceutical imaging material is one which will produce a positron or single photon emission.

In the embodiment depicted in FIGS. 1 and 2 and described herein, the distal end 16 of the flexible tubular lumen 12 is configured to be removably insertable in the visually opaque substance relative to the interior structure to be visualized. Thus, the distal end 16 of the flexible tubular lumen 12 may be configured and equipped with suitable means to facilitate insertion of the distal end 16 into the visually opaque substance. Preferably, such insertion facilitating means is capable of ensuring removable nondestructive insertion of the flexible lumen. As used herein, the term "nondestructive insertion" is taken to mean that the insertion process occurs without damage to the lumen and with minimal or no trauma to the material surrounding the region into which the lumen 12 is inserted. It is generally envisioned that the lumen 12 is inserted into a vessel or a channel within the body such as, but not limited to, the upper or lower gastrointestinal tract, genitourinary or head and neck tissues or the like. The device may be used so as to rest in or define potential spaces in the body. As an example, one particular anatomical region of interest which can be advantageously analyzed using the device of the present invention is the esophagus. As depicted in FIG. 1, the insertion means is a directional tip 18 which may include suitable lubricant and guiding surfaces thereon. Alternately, the insertion facilitating means may include various gels, weights, or other devices which permit and facilitate the traverse of the distal end 16 of the flexible tubular lumen 12 into position in the cavity to be visualized. In order to insert the device of the present invention into position in the visually opaque substance, the device 10 as depicted in FIGS. 1 and 2 can have a device which imparts additional temporary rigidity to the flexible lumen 12. One example of such a rigidity-imparting device would be a stylet or other thin rod.

Means for proper pressure equalization in the interior of the flexible tubular lumen 12 is also provided in the device 10 of the present invention, as required. As depicted in FIG. 1, pressure equalization means can include aperture 19 located near or adjacent to the distal end 16 of the flexible lumen 12.

The flexible tubular lumen 12 is composed of a suitable biologically stable and non-reactive substrate material. As used herein, the term "biologically stable" is taken to mean that the material of choice is one which is generally recognized as safe for use in biological and/or medical applications. Preferably, the flexible tubular lumen 12 is composed of a polymeric material. Examples of suitable polymeric materials include a polymer selected from the group consisting of SILASTIC®, polyurethane, silicone, polyvinyl chloride and mixtures thereof.

The material of choice will be one which provides sufficient dimensional flexibility to accommodate bending and/or torsion as would occur with the insertion and positioning of the device 10 into the appropriate cavity.

The material of choice may also be one which provided sufficient stability to support a potential space in the body. The material of choice also is one which will permit acquisition of a physically detectable signal from the imaging material and generation of a discernable image during the desired scanning process. By permitting acquisition of such a signal from the imaging material, it is contemplated that the material of choice, at minimum, will not interfere with production of a detectable signal, either by absorption, attenuation or interference with the signal or the signal generating medium or process or by any other means. It is also contemplated that the material of choice may be one which would enhance or augment the signal. The term "detectable signal" as used herein is defined as a transmitted, absorbed or transmittable signal which can be converted into a visual representation on film or a monitor screen by a suitable detector and associated detection process. This can involve the use of sound, photons, magnetic resonance or the like. The suitable detection device will be one which allows for visual representation of a physically detected signal change by the device of the present invention.

In the embodiment depicted in FIGS. 1 and 2, the flexible lumen 12 of the present invention will be composed of a polymeric material which is essentially transparent upon PET scan or SPECT scan. Ideally, the polymer of choice will be at least partially opaque under scans such as CT, MRI or ultrasound. The polymer of choice will be one which is capable of permitting the emission of a signal which can be detectable on the exterior of the visually opaque substance under study.

The material of choice may be capable of generating or emitting a detectable signal independent of any material contained in the lumen. At minimum, the material of choice is capable of permitting the transmission of a detectable signal from the interior of the lumen. Finally, the material of choice for the flexible tubular lumen 12 is one which prevents appreciable contact between the imaging material integrated or contained in the interior of flexible lumen 12 and the surrounding visually opaque material to be analyzed.

Thus, the material of choice will be one which provides biological isolation of imaging material contained in the lumen. By "biological isolation", it is meant that the material of choice prevents uptake of any appreciable amount of the imaging material into the surrounding material to be analyzed. The imaging material is self-contained by or within the lumen 12 in a manner which permits the removal of appreciably all imaging material upon completion of imaging procedures.

It is to be understood that the marker member will be a flexible or rigid tube, cylinder or solid as required by the anatomical region under analysis. The marker member itself can be capable of producing increased echogenicity for ultrasound imaging as a result of its internal architecture. The flexible or suitably rigid marker member can also be capable of producing a local magnetic field which can re-emit radiowaves which can be received for magnetic resonance image reconstruction. It is to be understood that the marker member can be capable of producing photon or positron emission for SPECT or PET imaging.

These features can be functions of the marker member itself rather than of material contained therein. Moreover, these features provide an image reconstructable signal in biological isolation as specified above.

Where the imaging material is a radiopharmaceutical material, the surrounding material to be studied exhibits little radiopharmaceutical uptake. In the embodiment shown in FIGS. 1 and 2, because the lumen 12 is capable of providing biological isolation between the imaging material and the surrounding visually opaque substance, the device 10 of the present invention can permit the use of concentrations and/or types of radiopharmaceutical or other imaging material which could not be easily employed otherwise due to sensitivity of the surrounding tissue or handling difficulty when used without the device 10.

The imaging material 17 is preferably contained in at least a portion of the hollow interior defined in tubular lumen 12. The imaging material 17 can be present in any suitable configuration and on any suitable substrate such as a movable rod, an amorphous solid, a liquid, or liquid suspension. The type of imaging material and substrate material are described in greater detail subsequently. In the preferred embodiment, the location of the imaging material is adjustable relative to the flexible lumen 12.

The imaging material 17 present in the device 10 of the present invention is a material which will provide a detectible signal as a form of absorption, echo, harmonics, magnetic resonance or emission characteristics of the imaging material which can be traced, recorded and analyzed in a manner which will provide the analyst with usable data. A radiopharmaceutical source material capable of producing particle emission may be employed. A material capable of producing positron and/or gamma emissions is most preferred due to its ready use with existing technology. While positron and/or gamma emitting materials are the most widely used to date, it is to be considered within the purview of this invention that other radiopharmaceutical source materials capable of producing other types of detectible emission may be successfully employed within the limitations defined in this invention.

Radiopharmaceutical imaging source material suitable for the present invention is preferably of a type which could be employed in PET or SPECT analysis procedures. Thus, various positron emission imaging source materials or single photon gamma emitting source materials are most preferred. Currently, preferred positron emission source material is of a type which will generate positron emission of the average path length in tissue, in a range between about 0.01 mm and about 2.0 cm, with a range between about 0.05 mm and about 7.0 mm being preferred. Single photon or gamma emitters generally evidence emission in a range between about 30 KeV and about 1000 KeV, with a range between about 60 KeV and about 700 KeV being preferred. It is to be understood that the general ranges noted are a function of the detection limits of the imaging device employed. Thus, the use of radiopharmaceutical source material having different or lower emissions is contemplated by the present invention upon advent of more powerful or sensitive emission collection, capture or detection device.

It should also be noted that the preferred range of emission for the radiopharmaceutical imaging material contained in the device will be affected by uptake of radiopharmaceutical material administered intravenously in conventional PET or SPECT imaging techniques. While it is contemplated that the device 10 of the present invention can be employed alone, it is also contemplated that the device 10 of the present invention can be employed as an adjunct with, or augmentation to, existing imaging techniques including, but not limited to, mammography.

In conventional PET/SPECT techniques, intravenously administered metabolic uptake material tagged with a radioisotope marker is delivered to the tissues of interest through the bloodstream. In conventional MRI techniques, contrast material is delivered to the tissues of interest through the bloodstream or into areas such as joint spaces. In ultrasound techniques, non-vascular contrast agents and targeted contrast agents may be administered into direct contact with a body cavity or blood vessel respectively. As such, the ultrasound contrast material is delivered to tissues of interest. In such techniques, the imaging material of the present invention will be selected to augment or complement the emission generated by the uptake material that is either placed in the joint regions or intravenously administered. Thus, the imaging material 17 contained in the device 10 of the present invention can be the same as the one administered intravenously or could be complementary to the intravenously administered material, as required by the parameters of the imaging procedure being conducted. It is to be considered within the purview of this invention that the imaging material employed in the device of the present invention could be "tuned" to accommodate, accentuate or provide a gradient scale against which biological areas of active emissions, due to cellular uptake of placed or intravenously administered imaging material, can be measured.

Thus, in the simplest application of the device of the present invention, the radiopharmaceutical imaging material 17 in the device 10 would have an emission range complementary to the emission range produced by the uptake of intravenously administered radiopharmaceutical imaging material by the tumor or tissue of interest. That is, the radiopharmaceutical imaging material employed in the device would emit at a sufficient intensity to provide localization of critical structures without impeding visualization of target tissue. In another use of the device of the present invention, the radiopharmaceutical imaging material would be tuned to provide a standard emission band against which the metabolic activity or molecular processes of the target tissue of interest could be more specifically analyzed. Differences between the standard known emission generated by the radiopharmaceutical material 17 in the device 10 and the emission produced by the target tissue could provide valuable information regarding structure, type and activity of the tissue of interest based on accumulated differential data and study.

As indicated, the imaging material 17 employed in the device 10 of the present invention need not be identical to radiopharmaceutical imaging material that is intravenously administered to achieve metabolic uptake necessary in a PET or SPECT scan. While it is envisioned that, in certain instances, advantages may accrue by employing the same radiopharmaceutical imaging material 17 in device 10 as is used as the intravenous metabolic uptake agent, it is also contemplated that the material employed in the device 10 of the present invention could differ from that employed in the intravenous metabolic uptake material. This could advantageously lead to use of different materials such as materials which exhibit a slower rate of radioactive decay that would be tolerated in an uptake situation. Additionally, it is anticipated that various positron or gamma emitting materials which do not readily tag to a biological marker material, such as glucose materials tagged with various radioisotopes, could be advantageously employed as the imaging material 17 in the present invention.

Various radiopharmaceutical imaging materials can be advantageously employed. These materials include 2-deoxy-2-[$^{18}$F]-fluoro-D-glucose in standard aqueous suspension. Other radioisotopes which can be employed in addition to flourine-18 include nitrogen-13, copper-62, technetium-99$_m$, indium-111, gallium-67, germanium-68, iodine-123, technetium-94, cesium-128, iodine-124, carbon-11 oxygen-15 and rubidium 82. It is to be understood that positron emitting radioisotopes other than the foregoing representative listed members may also be employed in the device of the present invention. Suitable materials will be those capable of being integrated into an appropriate molecular substrate carrier media so as to be integrated into a solution, suspension, colloid or solid. The resulting radiopharmaceutical imaging material may be a solution, suspension, colloid or solid prepared with a suitable organic, inorganic, biological, colloidal or native state material.

It is also within the purview of this invention to employ suitable contrast agents as the imaging material of choice. Such agents would be those which can be successfully employed in imaging techniques such as MRI, ultrasound, and the like. Examples of contrast agents that can successfully be employed in the marker member of the present invention include materials commonly referred to as gadolinium complexes such as diethylenetriamine pentaacetic acid. One such material, gadopentetate dimeglumine, is commercially available for medical use as an injectable contrast agent and is marketed under the trade name MAGNEVIST from Berlex Imaging. Gadopentetate dimeglumine has a density of 1.195 g/ml and a viscosity of 4.9 cP at 20 degrees C. and 2.9 cP at 37 degrees C. Other suitable contrast agents include vitamin E and CT materials such as diatrizoate sodium (commercially available under the trade name HYPAQUE) and iohexol (commercially available under the trade name OMNIPAQUE). Other materials would be apparent to those skilled in the art upon reading the disclosure of the present invention.

In the embodiment as illustrated in FIGS. 1 and 2, the radiopharmaceutical imaging material 17 is positioned in the inner cavity defined by inner wall 15 of the flexible tubular lumen 12. It is anticipated that the radiopharmaceutical imaging material 17 is contained in the flexible tubular lumen 12 in a manner which can facilitate its movement relative to the longitudinal axis of the flexible tubular lumen 12. In this embodiment, the radiopharmaceutical imaging material 17 is contained in a suitable substrate which can be translationally positioned along the longitudinal axis of the flexible tubular lumen 12 as desired. This substrate can be any material capable of movement relative to the longitudinal axis of the flexible tubular lumen 12. Thus, it is contemplated that the radiopharmaceutical imaging material 17 may be contained in a suitable polymeric rod or shaft (not shown) which is capable of translational movement relative to the tubular lumen 12. In such instances, the rod containing radiopharmaceutical imaging material therein or thereon may be separately insertable into the tubular lumen 12 after positioning of the lumen 12 in the cavity of the visually opaque substance to be imaged. Alternately, the rod containing the radiopharmaceutical imaging material may be employed as a flexible stylet which can be used during the initial positioning process. Because the rod is translationally moveable relative to the lumen 12, it is contemplated that the entire rod need not be visually active. A portion of the rod can be detectably active or capable of being rendered detectably active. This portion can be brought into the desired position by translational movement of the rod relative to the lumen 12 once the lumen 12 is in position in the subject. Where a removable rod containing radiopharmaceutical imaging material 17 is employed as part of the device 10 of the present invention, it is contemplated that the radiopharmaceutical imaging material 17 may be one which can be rendered detectably active by suitable excitation techniques prior to the positioning of the radiopharmaceutical imaging material in the subject. Alternately, the radiopharmaceutical imaging material is one which can be rendered detectable once the device is in place. As used herein, the term "rendered detectable" is defined as being made capable of providing a physically detected signal which can be translated into a suitable visual and/or mathematical or algorithmic representation. It is also within the scope of this invention that the rod, either flexible or rigid may be echogenic or capable of producing a magnetic resonance signal.

In MRI and ultrasound embodiments, as well as the radiopharmaceutical embodiment detailed herein, the imaging material is incorporated in a fluid or fluid-like substrate or carrier such as an aqueous or organic suspension, an aqueous or organic dispersion, an aqueous/organic emulsion, a gel, or an amorphous wax. The concentration of radiopharmaceutical imaging material in the substrate or carrier is generally an amount sufficient to provide an emission detectable external to the visually opaque substance and translatable into discernable data. A concentration of radiopharmaceutical imaging material between about 0.001 microcurie/ml and about $10^7$ microcurie/ml is generally contemplated, with a concentration between about 0.01 microcurie/ml and about 100.0 microcurie/ml being preferred.

The fluid-like substrate or carrier is generally one which has a density and viscosity in ranges which will permit the material to be movably positioned but maintained within the interior of the flexible tubular lumen 12 in the manner described subsequently.

In the radiopharmaceutical embodiment depicted herein, a solution, suspension or colloidal preparation containing the radiopharmaceutical imaging material attached to a suitable material which is organic, inorganic, biological or in its colloidal or native state, is employed. In such embodiments, it is anticipated that the concentration of a radiolabeled substance or substances, in the marker member of the present invention will have an activity that will be suitable for structure or tissue localization. Such activity concentration will be above background concentrations and activity. If SUR or SUV is used as a quantitative measure, such values of apparent activity, as displayed by the scanning device, will be 0.01 to 1000 times background, but generally in the range of the SUR or SUV of the target. Generally this value will be not greater than 10 times the target SUR or SUV and not less than 0.1 times the target, where the target is the tumor or other radiopharmaceutically-avid structure being displayed. It should be noted that the actual concentration of a tracer in the marker will vary depending on the lesion size and resolution of the imaging device, so as to allow the apparent SUV to be detectable. Such measures would be known to the skilled artisan upon reading the disclosure of the present invention.

The tagging of radiopharmaceutical imaging material to a suitable organic material, as is the case in materials such as 2-deoxy-2-[$^{18}$F]fluoro-D-glucose, is known to those skilled in the art. Preparation of dispersions containing radiopharmaceutical imaging material as well as preparation of suitable MRI imaging material or ultrasound imaging material useful in the device of the present invention would be known to the skilled artisan upon reading the disclosure of the present invention.

The radiopharmaceutical, MRI or ultrasound imaging material may also be contained by a suitable amorphous polymeric substrate such as a polymeric wax. In such situations, it is anticipated that the radiopharmaceutical imaging material will be dispersed within the polymeric material in a manner which will permit effective imaging of the device 10 when in position in the visually opaque substance.

One example of a suitable class of amorphous polymeric wax substrates include those produced by the admixture of a suitable radiopharmaceutical source material in solution with a low melting polymeric polyethylene glycol material such as a CARBOWAX. One such CARBOWAX-type material is commercially available from Union Carbide Corporation under the trade designation CARBOWAX-1450. Alternately, a gelatin admixture could be prepared in the manner outlined in Tilbury et al., "Reusable Gels for Germanium-68 Sources," 42 *Appl Radiation Trans*. pp 1111-1114 (1991). Suitable gelatins include those commercially available from sources such as Aldrich Chemical Corporation or Knox Gelatin Inc. The material produced has a density between about 0.0001 g/ml and about 30 g/ml. Preferably, the radiopharmaceutical imaging material is maintained within the amorphous polymer in a manner which is sufficiently homogeneous to ensure proper imaging with minimal or tolerable variation in the concentration of emission produced by the device 10 throughout its target length. The term "target length" is employed to define the longitudinal location in the flexible lumen 12 where the radiopharmaceutical imaging material is located during scanning procedures.

In the embodiment depicted in FIGS. 1 and 2, the tubular lumen 12 of the device 10 of the present invention need not contain radiopharmaceutical, MRI or ultrasound imaging material throughout its entire length. Rather, in the preferred embodiment of the present invention, the imaging material 17 can be located as required at a discrete portion of the length of the lumen 12. This discrete location will correlate with the particular region, target or critical structure which is to be identified and visualized. The ability to translationally position the radiopharmaceutical imaging material 17 relative to the length of the lumen 12 provides the ability to further minimize contact between the patient and imaging employed in the device 10 by movably limiting the location of the imaging material relative to critical structures on an as-required basis. It can also be appreciated that the total volume of radioisotope-containing or potentially hazardous material is also minimized. This reduces the total amount of hazardous material generated which will require suitable handling and, ultimately, disposal.

Because the device 10 of the present invention is removably insertable in the visually opaque substance, it can be appreciated that imaging material contained therein generally will be removed from the visually opaque substance upon completion of the scanning procedures. Removal from a human or mammalian subject means that the imaging material need not be metabolized and/or excreted by the subject as a means of removal. It can be appreciated that this feature may facilitate the use of a wider variety of imaging materials than heretofore contemplated. It is possible that materials which could not be employed due to patient sensitivity and/or difficulties in metabolizing or excreting imaging material may be successfully used in connection with the device of the present invention.

The device 10 of the present invention includes suitable means for obtaining proper longitudinal translational location of the imaging material 17 contained therein. Such translational means as depicted in FIGS. 1 and 2 will be described in greater detail subsequently.

The present invention also contemplates a device 10' shown in FIG. 3 which includes a second flexible tubular lumen 20 coaxially disposed interior to the tubular lumen 12. Use of a device 10' having a second interior lumen 20 provides greater ability to regulate the position of the imaging material 17 and greater versatility as to the manner in which the device 10' can be positioned relative to the visually opaque substrate.

In a second embodiment of the present invention, the first, or exterior, lumen 12 is generally flexible and expandable. The tubular lumen 20 is generally flexible and has an interior surface 22 and an opposed exterior surface 24. The interior tubular lumen 20 is generally of the same or similar length to that of the first or exterior lumen 12. The flexible tubular lumen 20 also includes a proximal end (not shown) which is near the proximal end 14 of lumen 12 and a distal end (not shown) which is near the distal end 16 of lumen 12.

The second tubular lumen 20 is coaxially disposed relative to the interior of the flexible lumen 12 with a void space defined between the exterior surface 24 of the second flexible tubular lumen 20 and the interior surface 15 of the first tubular lumen 12. Imaging material 17 can be disposed in the defined void space in contact between the exterior surface 24 of the flexible tubular lumen 20 and the interior surface 15 of the flexible tubular lumen 12. As with the first embodiment, device 10' includes suitable means for obtaining proper longitudinal translational location of the radiopharmaceutical imaging material 17 contained therein. Such means will be described in greater detail subsequently.

In device 10', the interior cavity defined by inner wall 22 of the second flexible tubular lumen 20 can be essentially hollow. The device 10' of the present invention can include suitable means for pressurizing or inflating the second lumen 20 such that the second lumen 20 expands and exerts pressure on the outer flexible tubular lumen 12 and the radiopharmaceutical imaging material 17 contained therebetween. The pressure exerted is sufficient to exteriorly expand the two lumina 12 and 20 to conform to the contours of the cavity into which the device 10' is inserted. Thus, if the device 10' is inserted into a potential space, expansion of the second flexible tubular lumen 20 of device 10' will permit the exterior surface of the device to adapt to the contours present in the interior of the potential space or other channel. This can permit enhanced localization of contours present in the specific body cavity or adjacent cavities or tissues for more accurate radiologic diagnosis, intervention or radiation treatment planning.

It is anticipated that such expansion or inflation can occur by any suitable means. Generally speaking, expansion will occur by the introduction of suitable pressurized gas. Once imaging has been completed, the interior lumen 20 can be depressurized. This permits contraction of the device 10' preparatory to removal from the subject. During expansion, the imaging material 17 remains in position between the two lumina 12, 20. Thus, in device 10', the imaging material 17 is contained in a substrate of sufficient viscosity to permit interposition of the imaging material 17 between the two lumina 12, 20 during the expansion cycle.

The double lumen device 10' of the present invention can also be employed in a non-expanded configuration. In such double lumen configuration, it is anticipated that a first imaging material 17 is contained in the channel defined between the lumina 12 and 20. A second imaging material can be positioned in the channel defined by interior wall 22 of the second flexible tubular lumen 20. The first and second imaging materials employed in the two channels can be any type which would be suitable for use in various imaging studies. These two materials can be varied as necessary for margin studies to be conducted. Thus, one material can be an echogenic material which would be visible upon ultrasonic scans. The material could also be a contrast material visible during CT scans, or a magnetically excitable material visible during magnetic resonance imaging scans. A second material could be a radiopharmaceutical imaging material such as those described previously. It is also within the purview of this invention that the radiopharmaceutical imaging material 17 could be employed in the interior channel, defined by inner wall of flexible tubular lumen 20, while the alternate imaging material is employed in the more exterior channel. However, the positioning of the two relative materials would be dictated by the needs of the particular imaging series being conducted.

Double lumen device 10' of the present invention has particular advantages when employed during multiple scanning techniques. The device 10' containing the various imaging materials could be positioned at a discrete location in the body to be imaged. Various imaging scans could be conducted without repositioning the device. Thus, the device 10' of the present invention could be employed as a consistent landmark throughout several various scans to provide an accurate landmark or verification for the ultimate fusion of the data generated by the various scanning techniques. It is also possible to construct one or both lumen of a material which is optically visible under one or more scanning techniques. Thus, the device 10, 10' of the present invention could provide a constant reference under multiple scanning techniques.

In the device 10, 10' of the present invention, it is anticipated that the imaging material 17 is held in place by a combination of equilibrium pressures present when the device is in position in the subject. Reference is made to FIG. 4 in which the various pressures are graphically illustrated. Further reference is directed to FIG. 5 in which FIG. 5A is a mathematical representation of the forces acting on the radiopharmaceutical imaging material aliquot at equilibrium. FIG. 5B is a mathematical representation of the forces acting on the imaging material aliquot as air is introduced into the lumen.

Referring to FIGS. 2 and 3, one can see that a material such as an FDG solution will remain between gas phases present in the interior of lumen 12 in the device 10 or within the space defined between lumens 12 and 20 in the device 10'. FDG of a defined density ($\rho$) and volume is introduced into lumen 12 having a defined total volume and radius (r). Once in position, the imaging material slug in the lumen 12 is acted on by pressure(P) already existing in the internal organ system. Where this organ is the esophagus and upper gastrointestinal tract, the pressure exerted on the lumen is that present in the stomach ($P_s$). General pressure in the lumen would be the atmospheric pressure of the surrounding area ($P_t$). At equilibrium, the forces present on the FDG aliquot will add to zero as defined in Equation I with the first term equaling the effect of the downward pull of gravity and the second term equaling the downward pressure in the tube. These two forces are counterbalanced by the upward pressure exerted from the stomach ($F_s$) and redefined in terms of the device of the present invention in Equation III.

As air is injected, the aliquot of FDG moves down the tube such that Z can be defined as set forth in Equation IV. In such instances, the upward pressure exerted by the stomach is significantly greater than that exerted by gravity. Thus, the gravity term ($V_f \rho g$) is negligible. It can be appreciated, in this situation where gravity is negligible, that the tube can be twisted or curled and oriented in any position. Thus, the patient in whom the device is positioned may be standing, supine or prone with no adverse effect on the location of the slug. Gravity will not affect results because it is a negligible factor in the equation compared to that exerted by stomach pressure. In such instances, the equation for Z can be simplified to $$Z = \frac{P_A V_A}{\pi r^2 P_s}$$

The device 10, 10' of the present invention will be of suitable length to permit insertion into the associated cavity or body lumen in the visually opaque substance. The length will be sufficient to position the distal end 16 beyond the region to be scanned and visualized, while the proximal end 14 extends beyond the orifice or access region into the associated cavity. The proximal end 14 extends beyond the orifice for a sufficient length to permit placement and anchoring of the device 10, 10'. In situations where visualization of a structure such as the esophagus is sought, the flexible lumen 12 will have a length sufficient to span the upper digestive tract from the oral cavity to the stomach. Various lengths are contemplated based upon the region to be visualized. Such lengths would be evident to the skilled artisan. The device 10, 10' will have a diameter sufficient to be readily inserted into the visually opaque substance in an essentially non-obstructive, nondestructive manner.

As mentioned previously, the device 10, 10' of the present invention also includes means for positioning the imaging material relative to the longitudinal length of the lumen 12. One such approach is shown in FIG. 1, positioning means 26 can include a three-way stopcock 28 with a male luer lock positioned in fluid communication with the proximal end 14 of lumen 12. A suitable metering device for introduction of the desired imaging material is releasably attached to one valve of three-way stopcock 28. As depicted in FIG. 1, the metering device is a suitable volume luer lock syringe 30. A measured amount of the imaging material of choice can be placed in syringe 30 and metered into the lumen 12 through an open channel in stopcock 28. Once the imaging material has been introduced into the lumen 12, the stopcock 28 can be manipulated to close the associated valve and provide fluid connection with a suitable gas metering device. As shown in FIG. 1, the gas metering device is syringe 32. A measured amount of air or other gaseous material contained in syringe 32 can be introduced into the lumen 12 to urge the introduced volume of imaging material into the longitudinal position on the lumen 12. The position of the volume of imaging material can be verified by mathematical measurement and by various imaging techniques. Once in position, the stopcock 28 can be closed, thereby preventing further movement of the imaging material relative to the lumen 12. Suitable imaging scans can be accomplished. Upon completion of the imaging scans, the imaging material can be drawn back out of the lumen 12 by reversing the process described. The imaging material can be drawn back into syringe 30 for suitable disposal.

It is to be understood that the syringes 30 and 32 can be removably positioned on stopcock 28. Thus, stopcock 28 provides access to lumen 12. Because syringes 30 and 32 can be removably positionable, it can be appreciated that various imaging materials can be introduced and withdrawn in series to provide proper imaging material for various scans without removing the device 10, 10' from position in the visually opaque substance.

Upon completion of the desired imaging scans and removal of the imaging material, the empty device can be removed from the subject and discarded in a suitable manner.

Having generally described the present invention, reference is made to various examples to further illuminate and expand upon the invention so described. It is submitted that these examples are for illustrative purposes only and are not to be construed as limitative of the invention described herein.

EXAMPLE I

Figure 6:
FIG. 6 is a photograph of an x-ray of a model of the device of FIG. 1 with arrows delineating position of imaging material.

Studies were conducted in order to determine the potential uptake by a surrounding substance of imaging materials contained in the device of the present invention. A 10-French tube having a length of 109 cm, composed of polyurethane (TECOTHANE), was charged with a 2% hypaque saline solution. X-ray studies of the device thus prepared demonstrated fluid placement without air pockets in the fluid column. A copy of this x-ray is presented in FIG. 6.

This study indicated that an introduced solution would remain in a single volume in an elongated tube without intervening air bubbles or the like.

EXAMPLE II

Three devices of the present invention were prepared according to the disclosure of the present invention. The devices were each 10-French polyurethane tubes of 109 cm$^2$. Each device was charged with 1.6 ml of 2-deoxy-2-[$^{18}$F]fluoro-D-glucose in suspension prepared to have a total activity of approximately 44.6 microcuries to yield an apparent tracer activity on PET greater than that of normal soft tissue.

Each device so prepared was fastened at its proximal end and allowed to suspend with a distal end in an Erlenmeyer flask filled with water. Each flask was mechanically moved to simulate body activity. At the end of one hour, radioactive counts of the flask water were taken and did not exceed total background radiation. From this data, it can be concluded that radioactive infiltration into the surrounding water from the device of the present invention did not occur. It could be concluded from these results that material introduced into the device of the present invention would be held in stable position therein. Based on the results of this test, it could be concluded that there would be no appreciable leakage of fluid from the tube, either through the distal end or as a result of exfiltration through the polymeric material.

EXAMPLE III

In order to simulate use of the device of the present invention on a test subject, the procedure was simulated in a phantom. A 109 cm 10-French enteral feeding tube was positioned at a location simulating a subject's esophagus. The associated stylet was removed from the tube and an AP chest x-ray of the simulation dummy(phantom) was taken to confirm proper placement of the tube.

After proper placement was ascertained, the access port cap was cut off and replaced with a suitable three-way stopcock with a male luer lock. The existing flushing port of the tube was capped. Two 3-ml luer-lock syringes were affixed to the two open ports of the stopcock. One syringe was charged with 1.6 ml of FDG prepared in the manner described in Example II. The other syringe was charged with 2 ml of air.

In order to charge the lumen, the stopcock handle was turned to block flow from the air-filled syringe and to open a channel to the FDG-filled syringe. Injection of 1.6 cubic centimeters of FDG into the tube was accomplished. The stopcock handle was then turned to block the empty FDG syringe and to open a channel to the air syringe. Two milliliters of air were injected into the tube. This produced a gas column which moved the FDG solution in the tube into alignment with the simulated cervical esophagus at an area just below the gastroesophageal junction. PET scans of the phantom demonstrated that visualization of the imaging material contained in the tube occurred at a level consistent with that which would occur with normal organ uptake.

EXAMPLE IV

While the device remained in the phantom simulation, computed tomography scans of the simulated organ were performed using the device as a reference landmark. The device employed for the CT scans was a General Electric 9800CT/T scanner with a Hi-Lite Advantage detector system.

PET scans were also conducted using a Siemens ECAT 921 EXACT. Ten minute emission acquisition scans were followed by ten minute transmission scans. Emission and transmission scans were taken at two bed positions, each encompassing 15 cm. Images were reconstructed with filtered-back projection with attenuation correction. Data generated by the two scans were fused. Good correlation between the data generated by PET and the data generated by CT were obtained indicating accuracy of the images generated by the fused data.

Figure 7:
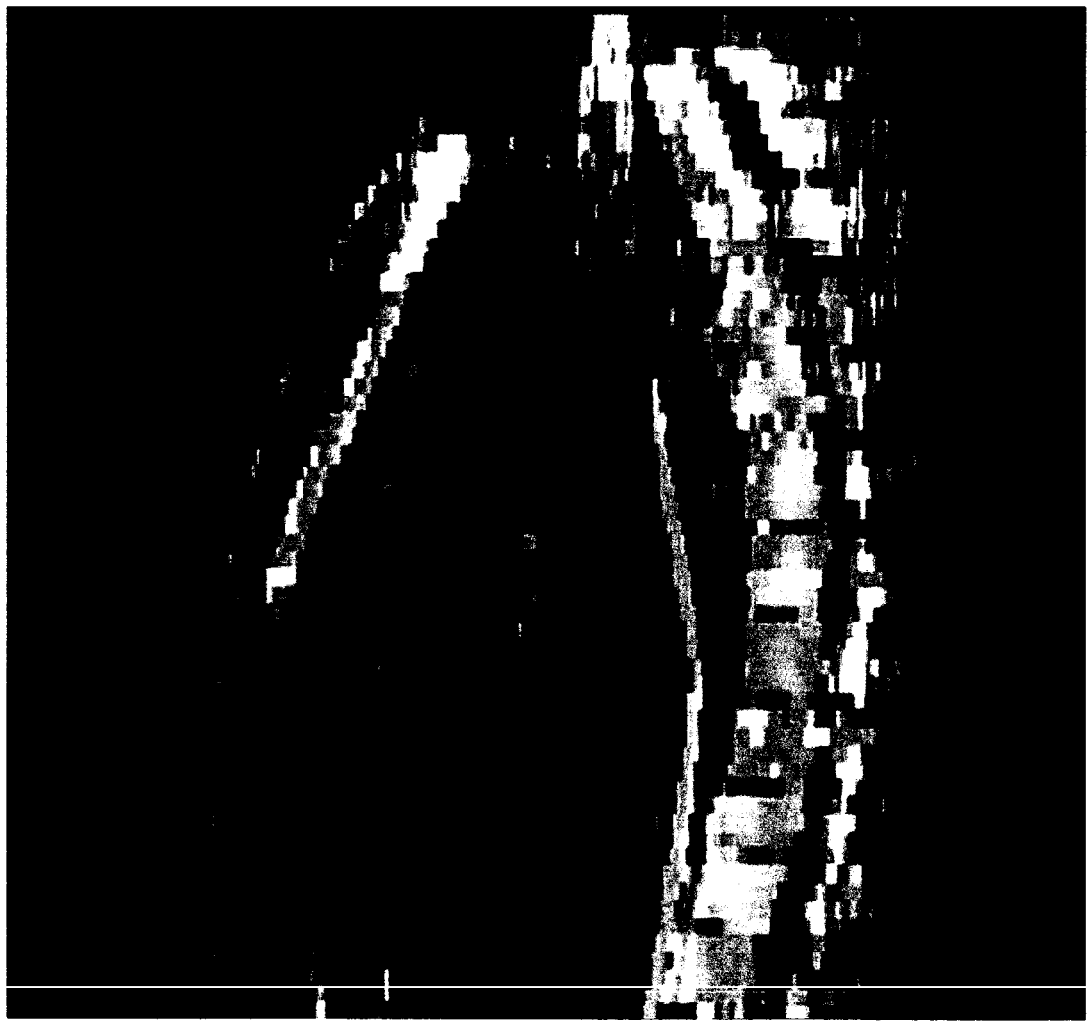
FIG. 7 is a sagittal view of fused CT and PET images taken of a phantom with the device of the present invention in position in the simulated region of the esophagus anterior to the vertebral bodies.

FIG. 7 demonstrates fused data of CT and PET scans taken along the sagittal view of the phantom. The device of the present invention can be seen in the lower three quarters of the scan extending horizontally through the location of the esophagus below the heart and liver in the phantom.

Figure 8A:
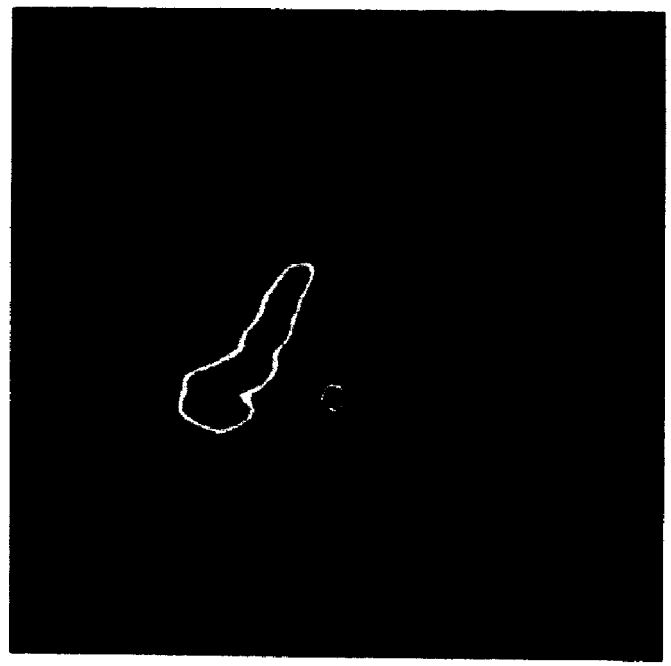
FIG. 8A is an axial view of a PET scan alone taken of the phantom of FIG. 7, this axial slice is superior to the heart in FIG. 7 with the device of the present invention in place in the simulated region of the esophagus.
Figure 8B:
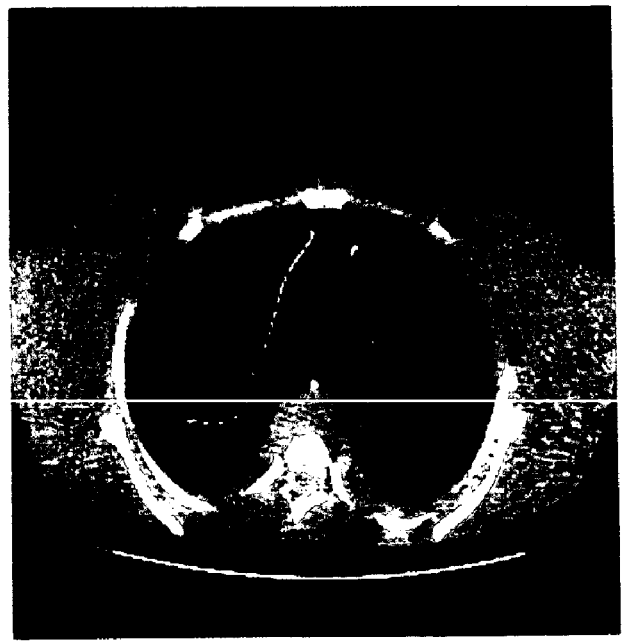
FIG. 8B is the view of FIG. 8A in CT scan with the device visible in the simulated location of the esophagus.
Figure 8C:
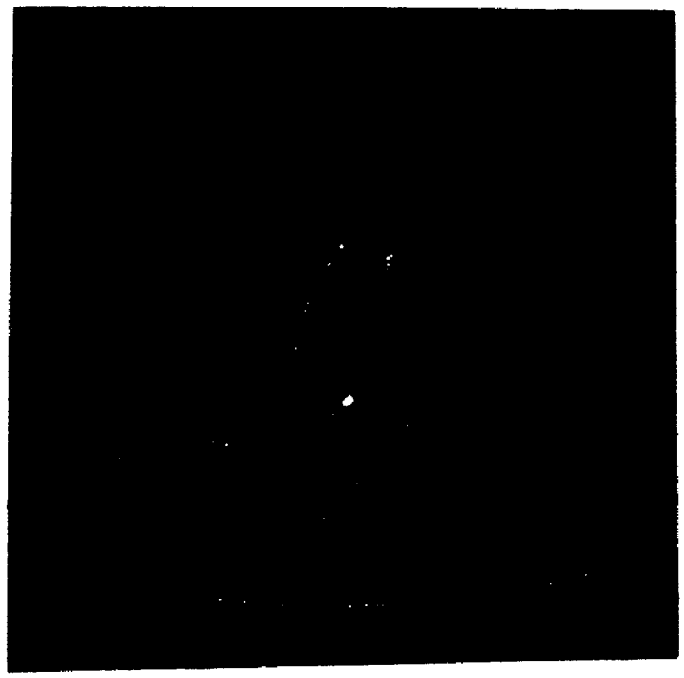
FIG. 8C is a fusion of the images derived from the scanning modalities of FIGS. 8A and 8B with the deep anatomy fiducial marker appearing yellow and located in the simulated location of the esophagus.

FIGS. 8A, 8B and 8C are axial slices of the phantom at a region at the base of the heart. The PET scan results are shown in FIG. 8A with the device of the present invention visualized as a circular region which appears red in color. The CT scan results demonstrate the vertebral body, rib, and void space indicating the lung with the device of the present invention appearing as a circular dot proximate to the vertebral body in a location simulating the esophagus. A fusion of PET and CT as shown in FIG. 8C permits accurate localization of structural elements visualized by PET relative to those visualized in CT and may also serve to verify the fusion technique.

Figure 9A:
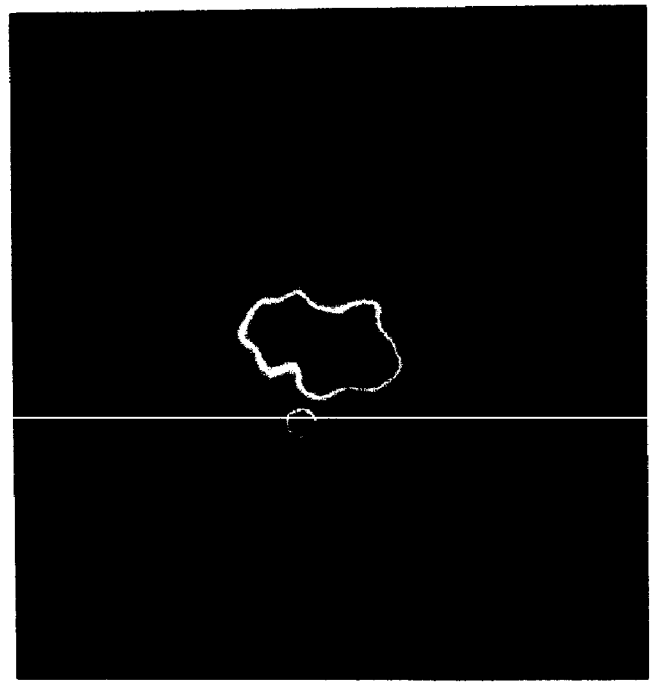
FIG. 9A is an axial view of PET scan taken distally to the axial view of the phantom in FIG. 7 with the device of the present invention in place in the simulated location of the esophagus.
Figure 9B:
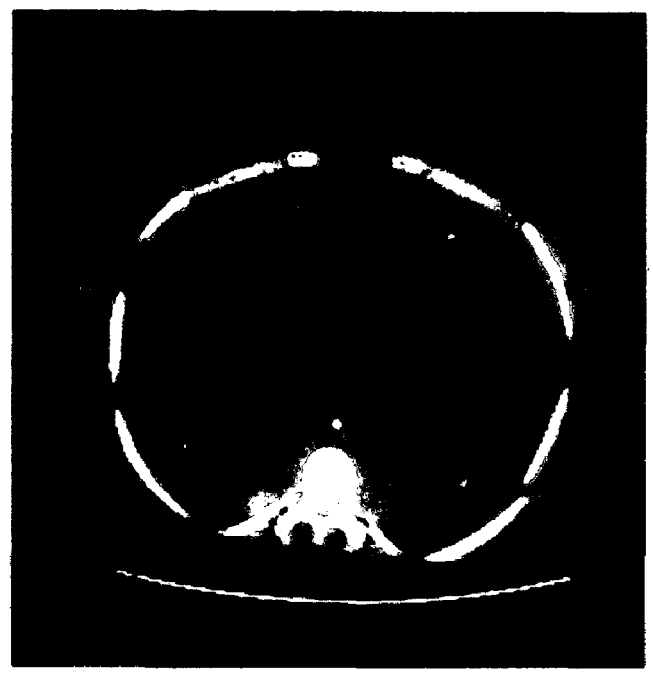
FIG. 9B is an axial view of a CT scan taken distally to the axial view of the phantom in FIG. 7 with the device of the present invention in place in the simulated location of the esophagus.

A second axial slice is presented in FIG. 9, taken distal to FIGS. 8A-C. PET image is set forth in FIG. 9A. The device of the present invention presents as the circular body in the lower third of the image. The device appears as the circular dot proximate to the vertebral body in the CT scan at FIG. 9B.

Figure 9C:
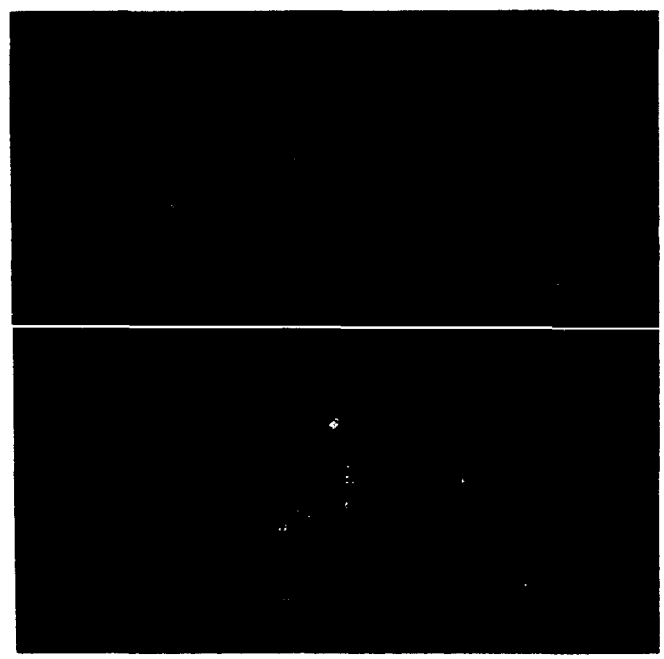
FIG. 9C is a fusion of the images derived from the scanning modalities of FIGS. 9A and 9B with the deep anatomy fiducial marker appearing yellow and being located in the simulated location of the esophagus.

It can be seen that the vertebral body, ribs and lung cavities are clearly pronounced in CT but essentially undifferentiated in PET, the methodology well-suited for visualization of many types of tumor tissue. Fusion of the two images, as shown in FIG. 9C provides a means for localizing metabolically active sites on PET against elements visualizable in CT.

Data generated from the PET scans were fused with data from CT analysis producing a three-dimensional representation of the esophageal simulation. Comparison of fused data against the simulation demonstrated accurate correlation between the various imaging modalities.

EXAMPLE V

Additional devices are prepared according to the disclosure of the present invention as outlined in Examples III and IV using a suitable gamma-emitting imaging material in the device. SPECT imaging procedures are performed and results generated are of similar resolution as those obtained for PET procedures. This indicates that the device of the present invention can include a gamma-emitting imaging material to be used in SPECT analysis.

The device of the present invention is also charged with a suitable imaging material which develops a magnetic moment and local magnetic field capable of radiowave re-emission which is received and reconstructed for MRI imaging; in this case a conventional dilute gadolinium contrast agent or a vitamin E solution or suspension is used as the imaging material. MRI scanning is conducted and a visually readable image of the esophageal simulation is produced. Such an image is fused with PET and CT images of the same with mutual information fusion software. Thus, the device of the present invention can be employed to augment, enhance and/or fuse to other imaging modalities. The fusion may be enhanced by the verification capacity of the device.

The device of the present invention, in position in the esophageal simulation, is charged with an ultrasonically dense contrast material. Ultrasonic studies are conducted of the esophageal simulation. Data generated is manipulated into a visually discernable image of the esophageal simulation. Thus, the device of the present invention can be employed to augment or enhance ultrasound studies.

This supports the conclusion that the device of the present invention can be configured to provide a marker and/or visualization aide and/or verification aide for a structure which lacks sufficient visualization ability under one or more scanning procedures. The device of the present invention may serve to verify and enhance the accuracy of fusion of multiple mutual imaging modalities for imaging fusion.

EXAMPLE VI

Fusion of data generated by the various imaging modalities outlined in Examples V, and VI is produced from the image data obtained by the nuclear medicine scans (PET and SPECT) and non-nuclear medicine imaging techniques (CT, MRI and ultrasound). Good correlation of data among the various scans and between scans and the esophageal simulation is obtained. This indicates that the images generated from the fused data can be used to ascertain and/or verify location and/or volume of structures of interest.

EXAMPLE VII

Devices according to the present invention are prepared each having a 10-French lumen of 109 cm in length. A male luer lock stopcock is located at the proximal end of the lumen with the distal end of the lumen configured similar to that of a conventional enteral feeding tube. Two 10 cc syringes are attached in releasable, sealable attachment to the valves of the stopcock. One such device, prepared according to the disclosure of the present invention, is placed in position in each respective patient using procedures for insertion and positioning of an enteral nasogastric feeding tube. The distal end terminates in the stomach of each patient. Upon insertion, the stopcock and associated syringes are located external to the patient. A portable AP chest x-ray is taken to ensure proper placement of the device relative to the gastrointestinal tract of the patient.

For purposes of this study, the patients on whom this test is performed are adults presenting with unresectable lung cancer which is treatable by radiation therapy. The cancer will be histologically confirmed to be locally advanced non-small cell lung cancer NSCLC), such as, squamous, large cell undifferentiated or adenocarcinoma. The patients on study will have disease limited to the thorax, adjacent mediastinum and neurovascular structures.

Once the device is in place and the patient is immobilized, the device will be loaded with 1.6 ml of FDG suspension with a total activity of approximately 44.6 microcuries to yield an apparent tracer actuary on PET greater than that of normal surrounding soft tissue, and a dose to be determined to be sufficient to assay in a Radioisotope Calibrator CRC 7-1214.

The FDG suspension will mark the areas of esophageal tissue during PET. In addition to the PET imaging material present in the device, each patient is also injected with an FDG imaging material after completing a four-hour fast according to the normal procedures for PET analysis. PET scans are then conducted. The patients are also subjected to CT-based radiation treatment planning. Fused CT-PET information were generated from the scans. Upon completion of the scan, the device was moved and the radiopharmaceutical material disposed of in a fashion appropriate for the handling of radioactive material.

Enhanced accuracy will be achieved relating to the location of both the target tissue and critical structures. More accurate estimations of the volume of critical structure and target tissue will also be achieved using the device of the present invention. Upon confirmation of the accuracy and reproducibility of such studies, it is anticipated that, in the future, such data will be provided to physicians for use in treatment planning and implementation.

As can be seen from the foregoing examples, the device of the present invention can be effectively employed in radiation treatment planning. One such disease site may be the lung. Patterns of failure analysis of radiation therapy alone for the treatment of inoperable or unresectable non-small cell lung cancer indicate that persistent or recurrent disease as well as distant metastases are significant problems. In order to combat this, combined regimens of chemotherapy and radiation therapy have been attempted. Additionally, the efficacy of delivery of more intensive radiation therapy has also been investigated. The addition of chemotherapy in lung cancer treatment has improved survival due, in part, to the decreasing frequency of distant metastases. Various studies have demonstrated that higher doses of radiation together with better tumor localization can be used to achieve better local control and survival for non-small cell lung cancer.

Radiation therapy for lung cancer is limited by normal tissue toxicity, including esophagitis, pneumonitis, cardiac toxicity, and spinal cord toxicity. Intense combined chemotherapy and radiation therapy or radiation dose escalation to the tumor target can increase the risk of normal tissue toxicity from the treatment itself. The device of the present invention allows visualization of normal tissue and identifies the location of the normal tissue. Localization of normal tissue can enhance three-dimensional radiation treatment planning (which uses CT imaging) as opposed to two-dimensional treatment planning (which uses x-ray imaging alone). Localization of normal tissue by the device enables measurement of radiation dose to normal tissue and improves radiation treatment plans by minimizing radiation dose to normal tissues.

The device of the present invention gives the added advantage of providing accurate internal landmarks for emission tomography such as PET or SPECT. Such landmarks can drive the registration of multiple data sets or serve as a means to verify the quality of a registration. The device provides the additional advantage in that it can be rendered opaque, resonant, or distinct to provide a landmark for other non-emission scanning methodologies. Thus, the device can provide an accurate, reproducible, and verifiable landmark for a variety of imaging techniques. The information that the device provides can be used to enhance both image registration and radiation treatment planning.

It is also believed that the device of the present invention can be employed in identification of other spaces or potential spaces in the body and, in so doing it provides the information to allow sparing of normal tissue from radiation toxicity to critical structures through more accurate radiation treatment planning. These spaces or potential spaces include the nasopharynx, oropharynx, as well as the rectum, colon, small bowel, stomach, vagina, vascular system and other structures. While the radiopharmaceutical material discussed in detail is FDG, it is to be understood that the radiopharmaceutical material could be a solid reusable source such as germanium-68 or a positron-emitting wire. It is also within the purview of this invention for the radiopharmaceutical material to be a material which can be excited into a positron-emitting state immediately prior to use. While materials having a relatively short half-life, such as FDG in suspension, are disclosed herein, it is within the purview of this invention for longer half-life materials to be employed as desired or appropriate. Radiopharmaceutical material will exist as a solution, suspension, colloid or solid which can be employed in conjunction with the removably insertable device of the present invention. The radiopharmaceutical material may be either reusable or disposable, depending upon the type of material and nature of its use, among other things. Similarly, the entire device of the present invention may be either reusable or disposable as required or dictated by the use of the device. Within the purview of this invention, it is understood that paramagnetic material or other materials capable of producing a local magnetic field that can re-emit radio waves that can be detected and used for reconstruction of a magnetic image, can be used as a signal-producing solution, suspension, colloid or solid for use in the removably insertable device of the present invention. The paramagnetic material may be either reusable or disposable depending upon the type of material and nature of its use, among other things. Similarly, the entire device of the present invention may be either reusable or disposable as required or dictated by the use of the device.

Within the purview of the present invention, it is also understood that echogenic material could be used in a suitable solution, suspension, colloid or solid. The echogenic material may be either reusable or disposable depending upon the type of material and nature of its use, among other things. Similarly, the entire device of the present invention may be either reusable, or disposable as required or dictated by the use to which the device is put.

It can be appreciated that this invention can be applied for use with imaging materials appropriate for use with PET, SPECT, MRI, ultrasound, and CT, as well as imaging modalities under development and variants of known and aforementioned modalities. The marker member of the device can have suitable configuration and a degree of rigidity or flexibility required by the nature of the region under study. The device can be used in a variety of anatomical sites as an internal marker, as a verification of image fusion or a tool or internal fiducial marker to drive fusion of multiple images.

High target-to-background contrast allows positron emission tomography using material and methodology such as 2-deoxy-2-[$^{18}$F]fluoro-D-glucose to detect lesions clearly. FDG-PET can detect and delineate neoplastic lesions more accurately than computed tomography (CT). Most current PET systems use high-energy photons from germanium-68 sources to measure photon attenuation of the body. This attenuation measure provides some anatomic information about specific areas of FDG uptake, but lacks the high quality morphological detail of CT, which uses lower energy x-ray photons. Determining by PET alone the precise anatomic location of lesions relative to normal structures can be challenging for applications such as radiation treatment planning or precise clinical cancer staging. Multi-modality image registration, which integrates the anatomic correlation provided by CT, addresses to some extent this limitation of PET. PET/CT scanners also can address this issue, but fusion of image sets can be imperfect due to patient motion.

Critical structures, also known as organs at risk, are normal tissues that unavoidably receive radiation dose along with target tissues during radiation therapy. Critical structures often alter radiation therapy beam arrangements and limit radiation dose to a target volume. As PET develops to complement radiation treatment planning, it may be useful to identify precisely the location of normal, but critical structures by PET alone.

Multi-modality or sequential image registration with PET is increasingly under study for target volume definition in radiation treatment planning. To be effective for radiation treatment planning, registration algorithms should take into account variability in patient positioning and displacement of internal organs from breathing, heart motion and normal tissue distortion from a tumor itself. Particularly for sequential imaging, registration techniques must account for changes in anatomy after surgery, patient size from weight loss or tumor dimensions after cytoreductive chemotherapy. These requirements suggest a need to verify the quality of registration and obtain information about registration-induced error in the fused product.

The internal marker device as disclosed herein can be utilized to demonstrate and identify normal tissues in PET and verify a mutual information registration algorithm.

Thus, the internal marker as disclosed herein can be employed to ascertain location of normal anatomical structures (the esophagus as an example) using imaging methods such as positron emission tomography. The deep anatomy marker utilizing a positron emitting material can extend the utility of positron emission tomography with materials such as FDG by providing a capacity to demonstrate selectively normal tissues by PET, an imaging modality generally considered to show function, not anatomy. Additionally, the internal marker serves as an intrinsic verification of a suitable automatic image registration method.

In the mutual information-based automatic registration algorithm, large voxel clusters in the bivariate histogram of gray values in referenced and reconstructed datasets, not associated with the few voxels corresponding to the marker, drive the registration algorithm. The internal marker serves to verify the image registration without biasing it. This eliminates much of the need to rely on how well a physician can judge registration mismatch. The small size and location of the marker in the body likely permits detection of a smaller error in a visually estimated center of marker by PET and the center of a region of interest such as the CT. The contribution to registration verification is an advancement that addresses a problem of image registration accuracy. Verifying registration is important for both PET and CT software and hardware based fusion approaches.

Identification of a normal structure such as the esophagus by PET permits approximation of critical structure location and volume through PET/CT image registration for CT or combined PET/CT radiation treatment planning. Three-dimensional conformal radiotherapy treatment planning systems may then compute and show the incidental 3D radiation dose distribution to a normal structure that may be difficult to localize by CT, such as the esophagus.

Use of the internal marker disclosed herein can assist in compensating for variations in anatomical shape. By way of non-limiting example, thoracic shape varies in space and time with the degree of periodicity of the cardiopulmonary cycle, which presents a complication for image registration. Use of an internal marker can reduce or eliminate such complications.

Combined PET/CT scanners can enhance target and normal tissue delineation. While PET/CT imaging helps demonstrate the esophagus, in some cases CT does not show the esophagus throughout its entire course without oral contrast. Such contrast can be problematic as it may degrade the quality of PET/CT imaging. In addition, despite the mechanically imposed image registration of PET/CT scanners, misregistration between the two data sets can and does occur because of patient motion. Unfortunately, the use of the CT for PET emission attenuation-correction forces the appearance of what purports to be excellent registration in the final emission reconstruction even in the presence of motion. One universally observed example of these motion-based artifacts is in the multiple appearance of the liver on CT at the level of the diaphragm due to respiratory motion. While most observers are accustomed to visualizing these artifacts, such artifacts are never seen in FDG emission studies, because of the temporal averaging protocols employed in PET acquisition. The motion artifact that now appears in new combined PET/CT scanner emission studies is a result of using the artifact-corrupted CT to attenuation-correct the averaged emission study. Other stealthy artifacts can result from patient motion, but are often not detected due to the apparent "excellent" registration in the final product. It has been found, quite unexpectedly, that the use of the marker member of the present invention in combined modality emission studies provides high contrast markers that can be used to verify image registration of combined modality scanners such as PET/CT. The use of such internal markers prevents hiding of misregistration by post-processing steps as previously described.

Thus, the internal marker, particularly one utilizing positron-emitting material, may have broad applicability for the verification of accuracy in multimodality and sequential image registration, or for assuring that regions of interest near the tumor are in register. Applications extend to identification by PET or SPECT of many other organs and potential anatomical spaces. The deep anatomy internal marker can also help optimize target volume definition and critical structure avoidance in radiation therapy treatment-planning algorithms that use image registration and PET.

It is contemplated that various multi-modality strategies can be employed utilizing the marker member described herein. The method of the present invention broadly contemplates a method for visualizing structure in a body comprising the step of registering a first image with a second image in which the first and second images include at least one region elucidated by a device removably inserted in the body.

The removably insertable device as broadly construed herein includes an interior, a proximal end, and a distal end. The distal end is removably insertable in the body. Preferred insertion is in proximate relationship to a cavity or potential space defined or present in the body. The cavity or potential space may include at least one of the oral cavity, nasopharynx, oropharynx, larynx, esophagus, rectum, uterus, urethra, vagina, urinary tract and gastrointestinal tract. The removably insertable device further includes an external access member contiguously connected to the proximal end of the marker member in which at least a portion of the external access member extends from the marker member to a location external to the body when the marker member is in removably insertable position in the body. Imaging material is contained relative to the marker member in a manner such that the imaging material does not directly contact the surrounding substance to be imaged. The imaging material of choice is one which produces a signal detectable external to the body.

As used herein the term "registration" is defined as a process whereby at least two images are brought together to create a combined image in which at least one feature region, structure, or element is more readily discernable and/or definable and/or quantifiable. It is contemplated that at least two images are registered in the method described herein. Multiple images may be registered as desired or required.

In the method described herein the first image is derived from at least one of PET and SPECT. The second image is derived from at least one imaging modality. Non-limiting examples of imaging modalities which can be employed to obtain the second image include, but are not limited to, MRI, CT, PET, SPECT, and ultrasound. It is contemplated that an image derived from PET may be registered with an additional image delivered from PET as desired and required. In situations where a first image derived from PET is registered with a second image derived from PET, it is contemplated that the imaging materials may be the same or may contain compositions having different radionuclides.

As used herein, the term "elucidated" is defined as defined or delimited in whole or in part. Thus the region of interest may be a potential space such as the esophagus into which the removable device may be inserted. Where various radionuclides are used in the multiple images, it is possible that elucidation of the region of interest may include registration of the first image with an image more precisely illuminating a region proximate thereto. In this way the region of interest can be more precisely characterized relative to other locations also visible in PET.

It is considered within the purview of the method of this invention to register or fuse multiple images derived from multiple imaging techniques provided that there are at least two images so registered. Thus, by way of non-limiting example it is contemplated that two different PET-derived images may be registered with a non-PET image, a PET-derived image with two non-PET images, etc.

As disclosed herein, the marker member may be associated with at least one critical structure. It is contemplated that the critical structure as that term is understood herein may be the region of interest elucidated by the marker member or one associated therewith.

It is also contemplated that the registration step can involve the registration of at least two concurrent images and/or the registration of at least two sequential images. Sequential images may be those taken in any suitable chronological and/or topographic sequence. Thus the present method is taken to facilitate time studies as well as cross-sectional views. More specifically, it is contemplated that a series of images can be fused in processes generally referred to as sequential image registration.

The method disclosed herein can be employed with the further step of implementing image registration verification methodologies that can include, but are not limited to, point fiducial matching and landmark-based image registration. Image registration verification can also include utilization of one or more mutual image-based automatic registration algorithm.

Examples of mutual image-based automatic registration algorithms include, but are not limited to, those contained in various automated information algorithm systems of which Mutual Information for Automatic Multimodality Image Fusion (MIAMI Fuse) is one example.

Suitable systems include those which permit registration of paired data sets by mapping images such as CT images or the like onto PET/SPECT attenuation images in a rigid-body, rotate-translate geometric transformation. In such systems, it is contemplated that the PET/SPECT data set can provide suitable reference geometry to run repeated automatic optimization that will cease when the mutual information objective function change is less than a predetermined level such as less than $10^{-3}$ bits with $10^{-4}$ bits being preferred.

In such systems, data set derived from CT or the like can be employed as the homologous data set permitting the software algorithm to interpolate the information derived from CT or the like into the special frame of the PET/SPECT data set. Using the same geometric transform, PET/SPECT emission images can be mapped onto the data set derived by CT or the like.

It is contemplated that the registration step can proceed as alignment of at least two intra-subject, intra-modality images. Such procedures include registration of images from the same subject acquired in the same modality. Non-limiting examples of such alignment or registration procedures step include PET to PET, SPECT to SPECT registration.

The registration can also proceed as alignment of at least two intra-subject, inter-modality images. Such procedures include registration of images of the same subject acquired in different modalities. Non-limiting examples can include registration of CT to PET, PET to SPECT, PET to MRI, etc. Also contemplated are PET to PET registration in situation where each PET has different radionuclide energies or activity distribution.

The registration step can also proceed as alignment of at least two inter-subject, inter-modality images. Such procedures include registration of images of different subjects acquired in different modalities. Non-limiting examples include registration of PET to a template such as MRI or the like.

While the invention has been described in connection with what is presently considered to be the most practical and preferred embodiment, it is to be understood that the invention is not limited to the disclosed embodiment but, on the contrary, is intended to cover various modifications and equivalent arrangements included within the spirit and scope of the appended claims, which scope is to be accorded the broadest interpretation so as to encompass all such modifications and equivalent structures as permitted under law.

What is claimed:

1. A device for visualizing a structure located on the interior of a visually opaque substance relative to a region of interest in a body, the device comprising:

a marker member, the marker member composed of a biologically stable material, the marker member configured to permit non-obstructive visualization, via positron emission tomography and single photon emission computed tomography, of at least one structure located relative to the region of interest, the marker member having an interior defining a lumen, a proximal end, and a distal end, the lumen being closed at the distal end, and the distal end of the marker member being removably insertable in the visually opaque substance in proximate relationship to a cavity of potential space defined therein;

an external access member contiguously connected to the proximal end of the marker member, at least a portion of the external access member extending from the marker member to a location external to the visually opaque substance when the marker member is in removable insertable position in the visually opaque substance, the external access member including a gas metering device;

an imaging material contained within the lumen via the closed distal end, such that the imaging material does not directly contact the visually opaque substance, wherein the imaging material produces a signal detectable external to the visually opaque substance, the imaging material containing at least one radiopharmaceutical material, the imaging material producing an image detectable by positron emission tomography and single photon emission computed tomography, the gas metering device configured to movably position the imaging material at a discrete location relative to a longitudinal plane of the marker member; and a pressure equalization member operatively connected to the lumen near or adjacent to the distal end.

2. The device of claim 1 wherein the imaging material is dispersed in an essentially homogenous manner through at least a portion of the interior of the marker member.

3. The device of claim 1 wherein the gas metering device is operable when the lumen is removably inserted in the visually opaque substance relative to the region of interest, and the gas metering device is located adjacent the proximal end of the lumen.

4. The device of claim 1 wherein the lumen is composed of a biologically stable material capable of permitting a non-obstructive visual image in and during the procedures that detect and translate the detectable signal resulting from the imaging material, such that the detection signal is sufficiently perceptible on the exterior of the substance to be imaged, the signal instrumentally detectable.

5. The device of claim 4 wherein the biologically stable material is one which prevents significant contact between the imaging material integrated or contained in the lumen and the surrounding visually opaque material.

6. The device of claim 1 wherein the lumen is at least partially flexible.

7. The device of claim 6, further comprising:

an interior lumen positioned coaxially interior to the flexible lumen at a defined interior diametric distance therefrom, the interior lumen defining a central inner cavity, wherein the interior lumen and the flexible lumen define a coaxial space therebetween, and wherein the imaging material is contained external to the interior lumen.

8. The device of claim 7, further comprising means for temporarily inflating the interior lumen and the associated outer flexible lumen into deformable contact with the visually opaque substance, the inflating means located external to the visually opaque substance.

9. The device of claim 1 wherein the visually opaque substance in which the device is adapted to be removably inserted includes an anatomical structure having a preexisting cavity of potential space, the cavity of potential space including at least one of oral cavity, nasopharynx, oropharynx, larynx, esophagus, uterus, urethra, vagina, urinary tract, gastrointestinal tract, and stomach.

10. The device of claim 1 wherein the imaging material is distributed in a flexible substrate material, the flexible substrate material being biologically non-reactive, stable and movably positionable relative to the interior of the marker member.

11. The device of claim 10 wherein the flexible substrate containing the imaging material is a fluid selected from the group consisting of water, propylene, glycol, and mixtures thereof.

12. The device of claim 10 wherein the flexible substrate containing the imaging material is a flexible, biologically compatible organic material selected from the group consisting of thermosetting polymers, thermoplastic polymers, waxes, organic sols, organic gels and mixtures thereof.

13. The device of claim 1 wherein the marker member has an interiorly oriented surface and an opposed exteriorly oriented surface, and wherein the imaging material is in contact with the interiorly oriented surface.

14. The device of claim 13 wherein the imaging material is bonded to the interiorly oriented surface of the marker member.

15. A device for visualizing an anatomical structure located in an interior of a visually opaque substance, the anatomical structure communicating with an external orifice, the device comprising:

a marker member, the marker member composed of a biologically stable material, the marker member having an interior defining a lumen, a proximal end, and a distal end, the lumen being closed at the distal end, and the distal end of the marker member configured to be removably insertable in the anatomical structure defined in the visually opaque substance;

an external access member contiguously connected to the proximal end of the marker member, at least a portion of the external access member extending from the marker member to a location external to the visually opaque substance when the marker member is in removably insertable position in the anatomical structure in the visually opaque substance, the external access member including a gas metering device;

an imaging material contained within the lumen via at least the closed distal end, such that the imaging material does not directly contact the anatomical structure, the imaging material being a radiopharmaceutical compound having a radioisotope capable of producing a positron decay product, the imaging material producing a signal detectable external to the visually opaque substance wherein the decay product produced by the radiopharmaceutical compound produces products of an energy spectrum of varying wavelengths including at least one of photons, electrons, annihilation photons and positrons, the products detectable by detection devices external to the visually opaque substance, the decay product detectable by positron emission tomography detectors and single photon emission computed tomography detectors, the gas metering device configured to movably position the imaging material at a discrete location relative to a longitudinal plane of the marker member; and a pressure equalization member operatively connected to the lumen near or adjacent to the distal end.

16. The device of claim 15 wherein the detectable decay product in generated by positron emission events and is detectable in a range between about 0.01 and about 2 cm.

17. The device of claim 15 wherein the anatomical structure visualized is at least one of oral cavity, nasopharynx, oropharynx, larynx, esophagus, rectum, uterus, urethra, vagina, urinary tract, and gastrointestinal tract.

18. The device of claim 17 wherein the radiopharmaceutical material produces a detectable gamma particle emission in a range between about 30 KeV and about 1000 KeV.

19. The device of claim 15, further comprising a second imaging material comprising a CT contrast agent.

20. The device of claim 19 wherein the CT contrast agent is selected from the group consisting of iohexol, diatrizoate sodium, and mixtures thereof.

21. The device of claim 15, further comprising a second imaging material comprising an MRI contrast agent.

22. The device of claim 21 wherein the MRI contrast agent is selected from the group consisting of gadopentate dimeglumine, gadolinium compounds, vitamin E containing compounds, and mixtures thereof.

23. A device for visualizing anatomical structures located on the interior of a biological system, the device comprising:
   a marker member, the marker member composed of a biologically stable material configured to permit non-obstructive visualization, via positron emission tomography and single photon emission computed tomography, of an anatomical structure of interest, the marker member having an interior defining at least one lumen, a proximal end, a distal end opposed to the proximal end, the at least one lumen being closed at the distal end, and the distal end removably insertable in a suitable cavity defined as an anatomical structure in the biological system;
   an external access member contiguously connected to the proximal end of the marker member, at least a portion of the external access member extending from the marker member to a location external to the biological system when the marker member is in removable insertable position in the biological system, the external access member including a gas metering device;
   an imaging material contained within the at least one lumen via at least the closed distal end, such that the imaging material does not directly contact the biological system, the imaging material producing a signal detectable external to the biological system and comprising at least one radiopharmaceutical material, the imaging material producing at least one decay product including at least one of photons, electrons, annihilation photons, and positrons, the product detectable by detection devices external to the biological system, the detectable product detectable by positron emission tomography detectors and single photon emission computed tomography detectors;
   the gas metering device configured to movably position the imaging material at a discrete location relative to a longitudinal plane of the marker member while the marker member is in position in the biological system; and
   a pressure equalization member operatively connected to the lumen near or adjacent to the distal end.

24. The device of claim 23 wherein the marker member is composed of a biologically stable material capable of permitting a non-obstructive visual image in and during imaging procedures which detect and translate the detectable signal resulting from the imaging material, such that the detection signal is sufficiently readable on the exterior of the substance to be imaged, and the signal is instrumentally detectable.

25. The device of claim 24, further comprising a second imaging material selected from the group consisting of:
   a. MRI contrast agents selected from the group consisting of paramagnetic compounds, and supermagnetic compounds;
   b. CT contrast agents selected from the group consisting of iohexol, diatrizoate sodium, and mixtures thereof;
   c. Ultrasound imaging materials; and
   d. mixtures thereof.

26. The device of claim 25 wherein the second imaging material is dispersed in an essentially homogenous manner through at least a portion of the interior of the marker member.

27. The device of claim 24 wherein the biologically stable material of the marker member is one which prevents significant contact between the imaging material integrated or contained in the marker member and the surrounding biological system.

28. The device of claim 23 wherein the at least one lumen comprises:
   an outwardly positioned, at least partially flexible lumen; and
   an interior lumen positioned coaxially interiorly to the outwardly positioned lumen at a defined diametric distance therefrom, the interior lumen defining a central interior cavity, wherein at least one imaging material is positioned at a location in the marker member.

29. The device of claim 28 wherein the imaging material is positioned at a location between the interior lumen and an interior surface of the outwardly positioned lumen.

30. The device of claim 29, further comprising:
   a second imaging material distinct from the imaging material contained between the outwardly positioned, at least partially flexible lumen and the interior lumen, the second imaging material contained in the central interior cavity in the interior lumen, wherein at least one of the imaging material and the second imaging material produces the signal detectable external to the biological system.

31. The device of claim 30, further comprising means for temporarily inflating the interior lumen and the outwardly positioned lumen into conforming contour with the cavity in the biological system.

32. A method for visualizing structure in a body, the method comprising:
   registering a first image with a second image, wherein the first image is derived from PET and SPECT, and the second image is derived from at least one of MRI, CT, or ultrasound, wherein the first and second images include at least one region of interest elucidated by a device removably inserted in the body, the removably inserted device including a marker member composed of a biologically stable material, wherein the marker member includes:
      a. an interior defining a lumen, a proximal end, and a distal end, the lumen being closed at the distal end, and the distal end of the marker member being removably insertable in the body in proximate relationship to a cavity or potential space defined therein;
      b. an external access member contiguously connected to the proximal end of the marker member, at least a portion of the external access member extending from the marker member to a location external to the body when the marker member is in a removably inserted position in the body, the external access member including a gas metering device;
      c. imaging material contained within the lumen via at least the closed distal end, such that the imaging material does not directly contact the substance to be imaged, wherein the imaging material produces a signal detectable external to the body, the gas metering device configured to movably position the imaging material at a discrete location relative to a longitudinal plane of the marker member; and
      d. a pressure equalization member operatively connected to the lumen near or adjacent to the distal end; and
   removing the marker member having the imaging material therein after recording the images.

33. The method of claim 32 wherein the marker member is associated with at least one critical structure.

34. The method of claim 32 wherein the registration step comprises registration of at least two sequential images.

35. The method of claim 32, further comprising verifying image registration.

36. The method of claim 35 wherein image registration verification includes at least one of point fiducial matching and landmark-based image registration.

37. The method of claim 35 wherein the image registration verification step comprises application of at least one mutual information-based automatic registration algorithm.

38. The method of claim 32 wherein the registration step further comprises alignment of at least two intra-subject, intra-modality images.

39. The method of claim 32 wherein the registration step further comprises at least two intra-subject, inter-modality images.

40. The method of claim 32 wherein the registration step further comprises at least two inter-subject, inter-modality images.

* * * * *